United States Patent
Ades et al.

(10) Patent No.: US 9,101,582 B2
(45) Date of Patent: Aug. 11, 2015

(54) USE OF A PNEUMOCOCCAL P4 PEPTIDE FOR ENHANCING OPSONOPHAGOCYTOSIS IN RESPONSE TO A PATHOGEN

(71) Applicant: The Government of the United States of America as represented by the Secretary of the Department of Health and Human Services, Centers for Disease Control and Prevention, Washington, DC (US)

(72) Inventors: Edwin W. Ades, Atlanta, GA (US); Gowrisankar Rajam, Tucker, GA (US); Sandra Steiner, Atlanta, GA (US); George M. Carlone, Stone Mountain, GA (US); Nikkol Melnick, Braselton, GA (US); Jacquelyn S. Sampson, College Park, GA (US); Joseph E. Martinez, McDonough, GA (US); Julie M. Skinner, Schwenksville, PA (US)

(73) Assignee: The United States of America as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 0 days.

(21) Appl. No.: 13/851,508

(22) Filed: Mar. 27, 2013

(65) Prior Publication Data
US 2013/0195893 A1 Aug. 1, 2013

Related U.S. Application Data

(62) Division of application No. 13/056,522, filed as application No. PCT/US2009/052384 on Jul. 31, 2009, now Pat. No. 8,431,134.

(60) Provisional application No. 61/085,208, filed on Jul. 31, 2008.

(51) Int. Cl.
| | |
|---|---|
| A61K 39/40 | (2006.01) |
| A61K 39/395 | (2006.01) |
| C07K 14/00 | (2006.01) |
| A61K 38/16 | (2006.01) |
| A61K 31/00 | (2006.01) |
| A61K 31/53 | (2006.01) |
| A61K 38/17 | (2006.01) |
| A61K 45/06 | (2006.01) |
| A61K 39/42 | (2006.01) |

(52) U.S. Cl.
CPC .............. *A61K 38/164* (2013.01); *A61K 31/00* (2013.01); *A61K 31/53* (2013.01); *A61K 38/1725* (2013.01); *A61K 39/395* (2013.01); *A61K 39/40* (2013.01); *A61K 39/42* (2013.01); *A61K 45/06* (2013.01)

(58) Field of Classification Search
CPC ... A61K 2300/00; A61K 31/00; A61K 31/53; A61K 38/164; A61K 38/1725; A61K 39/40; A61K 2039/505; A61K 39/00; A61K 39/395; A61K 39/42; A61K 45/06; C07K 14/3156
USPC .......... 424/190.1, 244.1, 184.1, 193.1, 242.1, 424/243.1; 530/300, 387.1, 825
See application file for complete search history.

(56) References Cited

U.S. PATENT DOCUMENTS 7,919,104 B2  4/2011  Ades et al.

FOREIGN PATENT DOCUMENTS

WO  WO 2006/127020  11/2006

OTHER PUBLICATIONS

Fischer et al 1990 Scand J Infect Dis Suppl (Abstract).*
Broun et al., "Catalytic Plasticity of Fatty Acid Modification Enzymes Underlying Chemical Diversity of Plant Lipids," *Science*, vol. 282, pp. 1315-1317, 1998.
Romero-Steiner et al., "Standardization of an opsonophagocytic assay for the measurement of functional antibody activity against *Streptococcus pneumoniae* using differentiated HL-60 cells," *Clinical and Diagnostic Laboratory Immunology*, vol. 4, No. 4, pp. 415-422, 1997.
Romero-Steiner et al., "Inhibition of pneumococcal adherence to human nasopharyngeal epithelial cells by anti-PsaA antibodies," *Clinical and Diagnostic Laboratory Immunology*, vol. 10, No. 2, pp. 246-256, 2003.
Seffernick et al., "Melamine Deaminase and Atrazine Chlorohydrolase: 98 Percent Identical but Functionally Different," *J. Bacteriol.*, vol. 183, pp. 2405-2410, 2001.

* cited by examiner

*Primary Examiner* — Padma V Baskar
(74) *Attorney, Agent, or Firm* — Klarquist Sparkman, LLP

(57) ABSTRACT

Methods for enhancing opsonophagocytosis of a pathogen of interest are disclosed. The disclosed methods include administering to a subject an isolated P4 peptide, which includes the amino acid sequence set forth as SEQ ID NO: 1 and optionally an isolated opsonic antibody or a fragment thereof that specifically binds to an antigen present on the surface of the pathogen of interest. In some examples isolated complement protein or a fragment thereof (for example, a C3a, C3b, iC3b, C3d, C4b, or C5a fragment of a complement protein) is also administered. Compositions containing isolated P4 peptide and one or more isolated opsonic antibodies or a fragment thereof that specifically binds to an antigen present on the surface of a pathogen of interest are also disclosed. In some examples, the compositions also include isolated complement protein or fragment thereof, such as one or more of C3a, C3b, iC3b, C3d, C4b, or C5a.

4 Claims, 6 Drawing Sheets

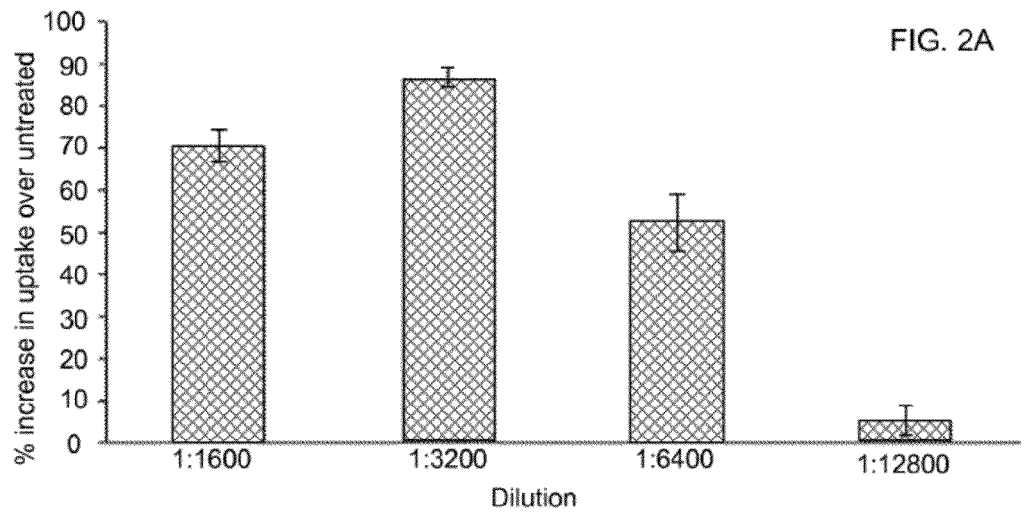
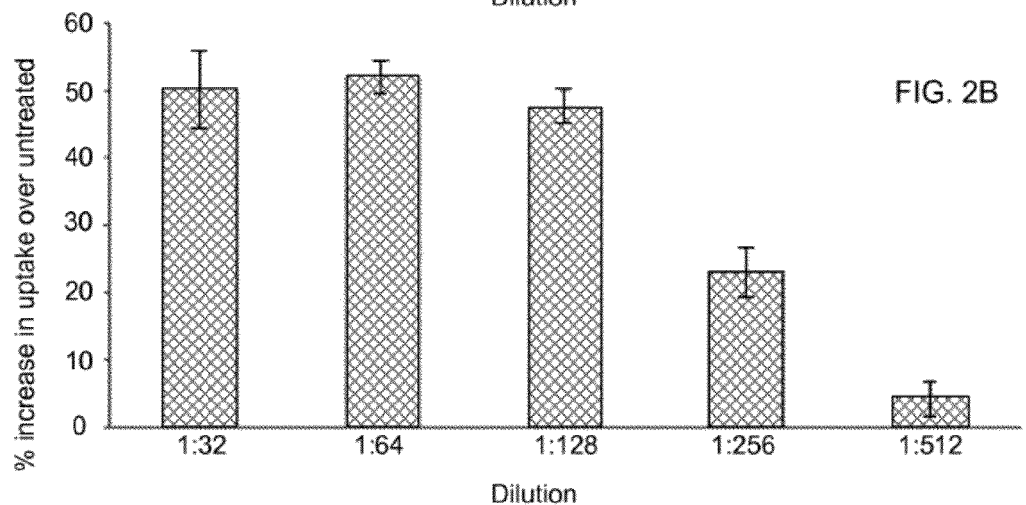
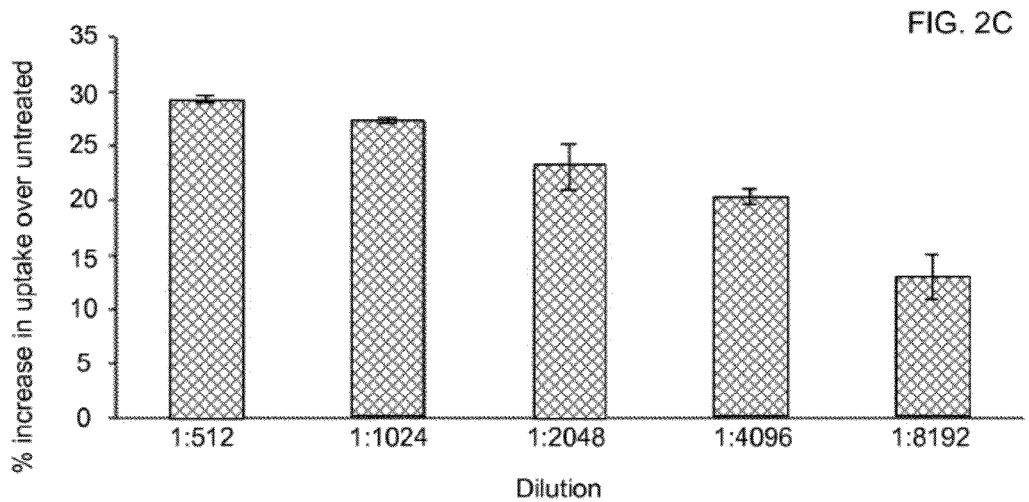

USE OF A PNEUMOCOCCAL P4 PEPTIDE FOR ENHANCING OPSONOPHAGOCYTOSIS IN RESPONSE TO A PATHOGEN

CROSS REFERENCE TO RELATED APPLICATIONS

This is a divisional of U.S. patent application Ser. No. 13/056,522, filed Jan. 28, 2011, now U.S. Pat. No. 8,431,134, issued Apr. 30, 2013, which is the §371 U.S. National Stage of International Application No. PCT/US2009/052384, filed Jul. 31, 2009, which was published in English under PCT Article 21(2), which in turn claims the benefit of U.S. Provisional Patent Application No. 61/085,208 filed on Jul. 31, 2008, all of which are incorporated herein by reference in their entirety.

FIELD

This disclosure relates to compositions and methods for the treatment and/or prevention of pathogenic infections and specifically to enhancing the effectiveness of opsonic antibodies in the opsonophagocytosis of pathogens.

BACKGROUND

Over the past century the development of agents to combat infections, such as viral infections, fungal infections, bacterial infections and the like, has vastly increased the average lifespan throughout the world. However, pathogens are increasingly developing ways to avoid or circumvent existing therapeutics. For example, the widespread use of traditional antibiotics, such as penicillin and related compounds has resulted in the development of bacteria that are resistant to these traditional antibiotics, as exemplified by the rise of methicillin resistant *Staphylococcus aureus* (MRSA). Similarly, viral pathogens, such as HIV, are able to acquire resistance to antivirals within a few replication cycles.

To combat the ever-changing landscape of pathogens and emerging resistance to the current therapies, the standard course of action for pharmaceutical companies is to develop an ever-increasing array of small molecule therapeutic agents. As an alternative, vaccines have been developed which stimulate the body to fight an infection by eliciting antibody responses to the target pathogen(s).

Antibodies protect against pathogen attack by recognizing and binding to antigens on the pathogen to facilitate the removal or "clearance" of the pathogens by a process called phagocytosis, wherein phagocytic cells (for example neutrophils and macrophages) identify, engulf, and subsequently destroy the pathogens. However, some pathogens, such as certain bacteria, can avoid phagocytosis. Bacteria can produce a "capsule" that inhibits phagocyte adherence. Opsonic antibodies overcome these defenses by binding to the capsule or to other target antigens on the bacterium, in a process called opsonization. This triggers the complement cascade, to produce a set of serum proteins with opsonic and lytic activities. Opsonic antibodies with complement components, such as C3a and C5a, bind the bacteria to make the bacteria extremely attractive to phagocytes and enhance the rate of clearance from the bloodstream. Recently, researchers have exploited opsonic antibodies by purifying opsonic antibodies and administering these antibodies to subjects in order to treat infections. While the use of opsonic antibodies has shown some promises in treating and/or preventing infection by pathogens, the need exists for enhancing the efficacy of these antibodies, for example to reduce the amount of the opsonic antibodies needed to achieve a therapeutically effective result. The methods disclosed herein meet those needs.

SUMMARY

The disclosed methods relate to enhancing the opsonic properties of opsonic antibodies to augment opsonophagocytosis of pathogens. This enhancement is based on the surprising discovery that P4 peptides, which include the amino acid sequence set forth as SEQ ID NO: 1, increase the ability of effector cells to internalize pathogens bound by opsonic antibodies. Because P4 peptides increase the ability of effector cells to opsonophagocytose pathogens bound by opsonic antibodies in a non-discriminate way, P4 peptides can potentially be used to target any pathogen of interest by using an opsonic antibody specific for any pathogen of interest. In specific examples, a P4 peptide is administered in conjunction with an opsonic antibody that is specific (for example specifically binds) for a selected pathogen of interest. Thus, the methods disclosed herein can be used to inhibit and/or treat an infection from any pathogen of interest.

The disclosed methods of enhancing opsonophagocytosis of a pathogen of interest in a subject include administering to the subject a therapeutically effective amount of an isolated P4 peptide that includes the amino acid sequence set forth as SEQ ID NO: 1. A therapeutically effective amount of an isolated opsonic antibody or a fragment thereof (or even multiple opsonic antibodies) that specifically binds an antigen present on the surface of the pathogen of interest can also be administered to the subject, for example to target a pathogen of interest. By administering the P4 peptide the opsonic activity of the opsonic antibody (whether the opsonic antibody is produced by the subject or administered to the subject) is increased, thereby enhancing the opsonophagocytosis of a pathogen of interest. In some examples of the disclosed method, isolated complement protein or a fragment thereof (for example, a C3a, C3b, iC3b, C3d, C4b, or C5a fragment of a complement protein) is also administered to the subject. In some embodiments of the disclosed method antibiotic is also administered to the subject.

The disclosed methods can be used to enhance the opsonophagocytosis of any pathogen of interest by using an opsonic antibody that binds to a selected pathogen of interest (or antibodies that bind to several pathogens of interest), for example bacterial pathogens of interest, viral pathogens of interest, virally infected cells, or fungal pathogens of interest, such as those set forth in the summary of terms. In specific examples, a pathogen of interest is *Streptococcus pneumoniae, Streptococcus pyogenes, Neisseria meningitides* or *Staphylococcus aureus*, such as methicillin resistant *Staphylococcus aureus* (MRSA). In some examples, the medicament is used to enhance the opsonophagocytosis of any pathogen of interest, for example in the treatment of an infection from a pathogen of interest, such as a bacterial pathogen of interest, viral pathogen of interest, virally infected cells, or fungal pathogen of interest, such as those set forth in the summary of terms.

Also disclosed are compositions, such as therapeutic compositions, for use in treating and/or inhibiting an infection by a pathogen of interest, for use in the manufacture of a medicament, and/or for use as medicament. The disclosed therapeutic compositions include a therapeutically effective amount of isolated P4 peptide including the amino acid sequence set forth as SEQ ID NO: 1 and a therapeutically effective amount of one or more isolated opsonic antibodies or a fragment thereof that specifically binds to an antigen present on the surface of a pathogen of interest. In some embodiments, the disclosed therapeutic compositions include a therapeutically effective amount of isolated complement protein or fragment thereof, such as one or more of C3a, C3b, iC3b, C3d, C4b, or C5a. In some embodiments the disclosed therapeutic compositions include a therapeutically effective amount of an antibiotic.

The foregoing and other objects, features, and advantages of the invention will become more apparent from the following detailed description, which proceeds with reference to the accompanying figures.

BRIEF DESCRIPTION OF THE DRAWINGS

FIG. 1A is a bar graph showing the effect of antibody concentration on opsonophagocytosis. At a 1:8 dilution of gamma globulin, opsonophagocytic killing (OPK) of Streptococcus pneumoniae serotype 3 (WU2) increased by 35% compared with control; this effect titrated out with dilution, paralleling the results obtained for controls at a 1:32 dilution. FIG. 1B is a bar graph showing the effect of complement on opsonophagocytosis. Baby rabbit complement was required for in vitro OPK, irrespective of the presence or absence of P4. The without-complement assay group received heat-inactivated complement (56° C. for 30 minutes). FIG. 1C is a bar graph showing the effect of P4 concentration on opsonophagocytosis. A gradual increase in the OPK of S. pneumonia serotype 3 (WU2) over control can be seen with the increase in P4 concentration. Gamma globulin at a 1:8 dilution was used as a source of serotype-specific IgG.

FIG. 2A-2C is a set of bar graphs demonstrating the P4-mediated enhancement of opsonophagocytosis in vitro as determined by flow cytometry. FIG. 2A is a bar graph demonstrating that P4 (100 µg/mL) increased the respiratory burst in HL-60-derived granulocytes. In-house quality control serum (QC2) was used to test the opsonophagocytic uptake (OPU) of OXYBURST®-labeled Streptococcus pneumoniae serotype 23F capsular polysaccharide (Ps)-coated beads by granulocytes. The OXYBURST® signal peaked at a serum dilution of 1:3200. FIG. 2B is a bar graph demonstrating that P4 (100 µg/mL) increased the OPU of S. pneumoniae serotype 14 Ps-coated beads by freshly isolated granulocytes from human blood in the presence of QC2. FIG. 2C is a bar graph demonstrating that P4 (100 µg/mL) increased the OPU of N. meningitidis A Ps-coated beads by HL-60-derived monocytes in the presence of in-house quality-control serum QC268.

SEQUENCES

Figure 1A:
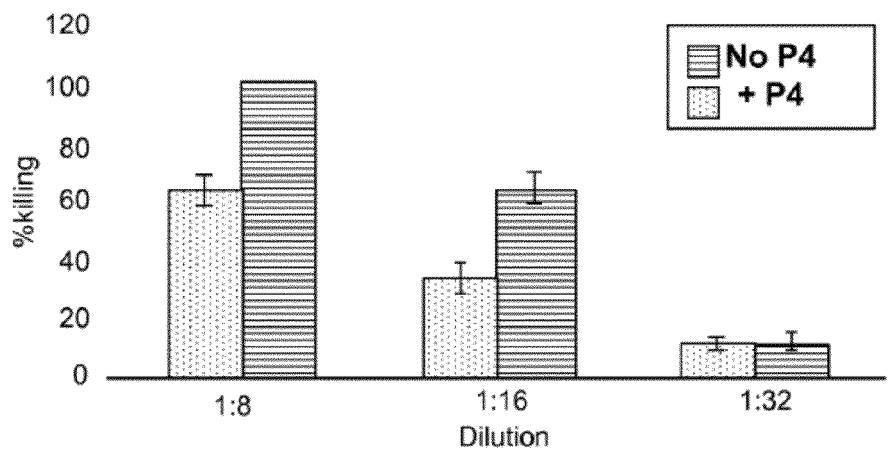
FIG. 1A-1C is a set of bar graphs demonstrating the P4-mediated enhancement of opsonophagocytosis in vitro.

The amino acid sequences listed in the accompanying sequence listing are shown using standard the three-letter code for amino acids.

The Sequence Listing is submitted as an ASCII text file in the form of the file named Sequence_Listing.txt, which was created on Mar. 25, 2013, and is 4,096 bytes, which is incorporated by reference herein.

SEQ ID NO: 1 is the amino acid sequence of an exemplary P4 peptide.

DETAILED DESCRIPTION

I. Summary of Terms

Unless otherwise noted, technical terms are used according to conventional usage. Definitions of common terms in molecular biology can be found in Benjamin Lewin, Genes VII, published by Oxford University Press, 1999; Kendrew et al. (eds.), The Encyclopedia of Molecular Biology, published by Blackwell Science Ltd., 1994; and Robert A. Meyers (ed.), Molecular Biology and Biotechnology: a Comprehensive Desk Reference, published by VCH Publishers, Inc., 1995; and other similar references.

As used herein, the singular forms "a," "an," and "the," refer to both the singular as well as plural, unless the context clearly indicates otherwise. For example, the term "P4 peptide" includes single or plural peptides and can be considered equivalent to the phrase "at least a P4 peptide."

As used herein, the term "comprises" means "includes." Thus, "comprising a P4 peptide" means "including a P4 peptide" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Administration: The introduction of a composition into a subject by a chosen route. For example, if the chosen route is intravenous, the composition is administered by introducing the composition into a vein of the subject. Similarly, if the route of administration is intranasal, the composition is administered through the nose.

Animal: A living multi-cellular vertebrate or invertebrate organism, a category that includes, for example, mammals and birds. The term mammal includes both human and non-human mammals. Similarly, the term "subject" includes both human and veterinary subjects, such as non-human primates. Thus, administration to a subject can include administration to a human subject. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Antibiotic: A compound, composition, or substance that inhibits the growth and/or kills bacteria. The term antibiotic can also be used to refer to more than one antibiotic. Examples of antibiotics that can be used with the methods and compositions of this disclosure include without limitation, aminoglycosides (such as amikacin, gentamicin, kanamycin, neomycin, netilmicin, streptomycin, tobramycin, and paromomycin); ansamycins (such as geldanamycin, and herbimycin); carbacephems (such as loracarbef, ertapenem, doripenem, imipenem/cilastatin, and meropenem); cephalosporins (such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and ceftobiprole); glycopeptides (such as teicoplanin and vancomycin); macrolides (such as azithromycin, clarithromycin, dirithromycin, erythromycin, roxithromycin, troleandomycin, telithromycin, and spectinomycin); monobactams (such as aztreonam); penicillins (such as amoxicillin, ampicillin, azlocillin, carbenicillin, cloxacillin, dicloxacillin, flucloxacillin, mezlocillin, meticillin, nafcillin, oxacillin, penicillin, piperacillin, and ticarcillin); polypeptides (such as bacitracin, colistin, and polymyxin b); quinolones (such as ciprofloxacin, enoxacin, gatifloxacin, levofloxacin, lomefloxacin, moxifloxacin, norfloxacin, ofloxacin, trovafloxacin, grepafloxacin, and sparfloxacin); sulfonamides (such as mafenide, prontosil (archaic), sulfacetamide, sulfamethizole, sulfanilimide (archaic), sulfasalazine, sulfisoxazole, trimethoprim, and trimethoprim-sulfamethoxazole); tetracyclines (such as demeclocycline, doxycycline, minocycline, oxytetracycline, and tetracycline); and others (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin, thiamphenicol, and tinidazole).

Antigen: A compound, composition, or substance that can stimulate the production of antibodies (such as functional antibodies) or a T-cell response in a mammal, including compositions that are injected, absorbed or otherwise introduced into a mammal. Examples include, but are not limited to, peptides, lipids, polysaccharides, and nucleic acids containing antigenic determinants, such as those recognized by an immune cell. In some examples, antigens include peptides derived from a pathogen of interest. Exemplary pathogens include bacteria, fungi, viruses and parasites. An antigen from a pathogen of interest can be used to produce an opsonic antibody that specifically binds to the pathogen of interest and participate in the opsonophagocytosis of the pathogen.

Antibody: Immunoglobulins and immunologically active portions ("fragments") thereof, such as molecules that include an antigen binding site that specifically binds (immunoreacts with) an antigen. A naturally occurring antibody (such as IgG, IgM, and IgA) includes four polypeptide chains, two heavy (H) chains and two light (L) chains interconnected by disulfide bonds. Examples of immunologically active portions thereof, include, but are not limited to, Fab, Fab', F(ab')$_2$, Fabc and Fv portions. Functional antibodies are antibodies that specifically bind to an antigen, for example an antigen present in the surface of a pathogen, can efficiently allow for complement fixation, and also interact with an effector cell, wherein the interaction of the antibody and effector cell results in internalization of the antibody by the effector cell and opsonophagocytosis of the pathogen.

Bacterial pathogen: A bacteria that causes disease (pathogenic bacteria). Examples of pathogenic bacteria against which opsonophagocytosis can be enhanced in accordance with the disclosed methods include without limitation any one or more of (or any combination of) *Acinetobacter baumanii, Actinobacillus* sp., *Actinomycetes, Actinomyces* sp. (such as *Actinomyces israelii* and *Actinomyces naeslundii*), *Aeromonas* sp. (such as *Aeromonas hydrophila, Aeromonas veronii biovar sobria (Aeromonas sobria),* and *Aeromonas caviae), Anaplasma phagocytophilum, Anaplasma marginale, Alcaligenes xylosoxidans, Acinetobacter baumanii, Actinobacillus actinomycetemcomitans, Bacillus* sp. (such as *Bacillus anthracis, Bacillus cereus, Bacillus subtilis, Bacillus thuringiensis,* and *Bacillus stearothermophilus), Bacteroides* sp. (such as *Bacteroides fragilis), Bartonella* sp. (such as *Bartonella bacilliformis* and *Bartonella henselae, Bifidobacterium* sp., *Bordetella* sp. (such as *Bordetella pertussis, Bordetella parapertussis,* and *Bordetella bronchiseptica), Borrelia* sp. (such as *Borrelia recurrentis,* and *Borrelia burgdorferi), Brucella* sp. (such as *Brucella abortus, Brucella canis, Brucella melintensis* and *Brucella suis), Burkholderia* sp. (such as *Burkholderia pseudomallei* and *Burkholderia cepacia), Campylobacter* sp. (such as *Campylobacter jejuni, Campylobacter coli, Campylobacter lari* and *Campylobacter fetus), Capnocytophaga* sp., *Cardiobacterium hominis, Chlamydia trachomatis, Chlamydophila pneumoniae, Chlamydophila psittaci, Citrobacter* sp. *Coxiella burnetii, Corynebacterium* sp. (such as, *Corynebacterium diphtheriae, Corynebacterium jeikeum* and *Corynebacterium), Clostridium* sp. (such as *Clostridium perfringens, Clostridium difficile, Clostridium botulinum* and *Clostridium tetani), Eikenella corrodens, Enterobacter* sp. (such as *Enterobacter aerogenes, Enterobacter agglomerans, Enterobacter cloacae* and *Escherichia coli,* including opportunistic *Escherichia coli,* such as enterotoxigenic *E. coli,* enteroinvasive *E. coli,* enteropathogenic *E. coli,* enterohemorrhagic *E. coli,* enteroaggregative *E. coli* and uropathogenic *E. coli) Enterococcus* sp. (such as *Enterococcus faecalis* and *Enterococcus faecium) Ehrlichia* sp. (such as *Ehrlichia chafeensia* and *Ehrlichia canis), Erysipelothrix rhusiopathiae, Eubacterium* sp., *Francisella tularensis, Fusobacterium nucleatum, Gardnerella vaginalis, Gemella morbillorum, Haemophilus* sp. (such as *Haemophilus influenzae, Haemophilus ducreyi, Haemophilus aegyptius, Haemophilus parainfluenzae, Haemophilus haemolyticus* and *Haemophilus parahaemolyticus, Helicobacter* sp. (such as *Helicobacter pylori, Helicobacter cinaedi* and *Helicobacter fennelliae), Kingella kingii, Klebsiella* sp. (such as *Klebsiella pneumoniae, Klebsiella granulomatis* and *Klebsiella oxytoca), Lactobacillus* sp., *Listeria monocytogenes, Leptospira interrogans, Legionella pneumophila, Leptospira interrogans, Peptostreptococcus* sp., *Mannheimia hemolytica, Moraxella catarrhalis, Morganella* sp., *Mobiluncus* sp., *Micrococcus* sp., *Mycobacterium* sp. (such as *Mycobacterium leprae, Mycobacterium tuberculosis, Mycobacterium paratuberculosis, Mycobacterium intracellulare, Mycobacterium avium, Mycobacterium bovis,* and *Mycobacterium marinum), Mycoplasm* sp. (such as *Mycoplasma pneumoniae, Mycoplasma hominis,* and *Mycoplasma genitalium), Nocardia* sp. (such as *Nocardia asteroides, Nocardia cyriacigeorgica* and *Nocardia brasiliensis), Neisseria* sp. (such as *Neisseria gonorrhoeae* and *Neisseria meningitidis), Pasteurella multocida, Plesiomonas shigelloides. Prevotella* sp., *Porphyromonas* sp., *Prevotella melaminogenica, Proteus* sp. (such as *Proteus vulgaris* and *Proteus*

*mirabilis*), *Providencia* sp. (such as *Providencia alcalifaciens*, *Providencia rettgeri* and *Providencia stuartii*), *Pseudomonas aeruginosa*, *Propionibacterium acnes*, *Rhodococcus equi*, *Rickettsia* sp. (such as *Rickettsia rickettsii*, *Rickettsia akari* and *Rickettsia prowazekii*, *Orientia tsutsugamushi* (formerly: *Rickettsia tsutsugamushi*) and *Rickettsia typhi*), *Rhodococcus* sp., *Serratia marcescens*, *Stenotrophomonas maltophilia*, *Salmonella* sp. (such as *Salmonella enterica*, *Salmonella typhi*, *Salmonella paratyphi*, *Salmonella enteritidis*, *Salmonella cholerasuis* and *Salmonella typhimurium*), *Serratia* sp. (such as *Serratia marcesans* and *Serratia liquifaciens*), *Shigella* sp. (such as *Shigella dysenteriae*, *Shigella flexneri*, *Shigella boydii* and *Shigella sonnei*), *Staphylococcus* sp. (such as *Staphylococcus aureus*, *Staphylococcus epidermidis*, *Staphylococcus hemolyticus*, *Staphylococcus saprophyticus*), *Streptococcus* sp. (such as *Streptococcus pneumoniae* (for example chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, erythromycin-resistant serotype 14 *Streptococcus pneumoniae*, optochin-resistant serotype 14 *Streptococcus pneumoniae*, rifampicin-resistant serotype 18C *Streptococcus pneumoniae*, tetracycline-resistant serotype 19F *Streptococcus pneumoniae*, penicillin-resistant serotype 19F *Streptococcus pneumoniae*, and trimethoprim-resistant serotype 23F *Streptococcus pneumoniae*, chloramphenicol-resistant serotype 4 *Streptococcus pneumoniae*, spectinomycin-resistant serotype 6B *Streptococcus pneumoniae*, streptomycin-resistant serotype 9V *Streptococcus pneumoniae*, optochin-resistant serotype 14 *Streptococcus pneumoniae*, rifampicin-resistant serotype 18C *Streptococcus pneumoniae*, penicillin-resistant serotype 19F *Streptococcus pneumoniae*, or trimethoprim-resistant serotype 23F *Streptococcus pneumoniae*), *Streptococcus agalactiae*, *Streptococcus mutans*, *Streptococcus pyogenes*, Group A streptococci, *Streptococcus pyogenes*, Group B streptococci, *Streptococcus agalactiae*, Group C streptococci, *Streptococcus anginosus*, *Streptococcus equismilis*, Group D streptococci, *Streptococcus bovis*, Group F streptococci, and *Streptococcus anginosus* Group G streptococci), *Spirillum minus*, *Streptobacillus moniliformi*, *Treponema* sp. (such as *Treponema carateum*, *Treponema petenue*, *Treponema pallidum* and *Treponema endemicum*, *Tropheryma whippelii*, *Ureaplasma urealyticum*, *Veillonella* sp., *Vibrio* sp. (such as *Vibrio cholerae*, *Vibrio parahemolyticus*, *Vibrio vulnificus*, *Vibrio parahaemolyticus*, *Vibrio vulnificus*, *Vibrio alginolyticus*, *Vibrio mimicus*, *Vibrio hollisae*, *Vibrio fluvialis*, *Vibrio metchnikovii*, *Vibrio damsela* and *Vibrio furnisii*), *Yersinia* sp. (such as *Yersinia enterocolitica*, *Yersinia pestis*, and *Yersinia pseudotuberculosis*) and *Xanthomonas maltophilia* among others.

Cell: A plant, animal, insect, bacterial, or fungal cell.

Conservative amino acid substitutions providing functionally similar amino acids are well known in the art. The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Not all residue positions within a protein will tolerate an otherwise "conservative" substitution. For instance, if an amino acid residue is essential for a function of the protein, even an otherwise conservative substitution may disrupt that activity.

Complement: A plasma protein system involved in immune defense. Following activation by antigen-antibody complexes, complement proteins lyse antigenic cells, attract phagocytic cells, and assist in the destruction of antigenic cells by opsonophagocytosis. In mammals, the complement system is made up of a series of about 25 proteins that work to "complement" the activity of antibodies in destroying bacteria, either by facilitating opsonophagocytosis or by puncturing the bacterial cell membrane. Complement also helps to rid the body of antigen-opsonic antibody complexes, for example by clearance of a pathogen that is bound by the opsonic antibody.

Complement proteins circulate in the blood in an inactive form. When the first of the complement substances is triggered-usually by antibody interlocked with an antigen. As each component is activated in turn, it acts upon the next in a precise sequence of carefully regulated steps known as the "complement cascade."

Complement fragments (such as C3a, C3b, iC3b, C3d, C4b, or C5a, which become bound to antigen during complement activation) trigger opsonophagocytosis by binding to specific cell-surface receptors (such as Fc receptors and C3b receptors on neutrophils and macrophages, and C3d receptors on macrophages). In some examples, the activity of an effector cells for opsonophagocytosis of antibody/antigen complexes is enhanced by the presence of P4 peptides.

Effector cells: Cells capable of binding to antibody/antigen complexes and internalizing such complexes. In particular examples, effector cells express Fc receptors, such as FcγRI, FcγRII and FcγRIII that bind to antibody/antigen complexes and facilitate internalization. In some examples, effector cells are derived from the serum of an individual (such as peripheral blood leukocytes, PBLs) or from an in vitro culture. Examples of effector cells include, but are not limited to: macrophages, mononuclear phagocytes, natural killer cells, and granulocytes such as neutrophils and eosinophils. In a particular example, the effector cell is a differentiated human promyelocytic leukemia cell, such as a differentiated HL-60 cell.

Epitope: An antigenic determinant. These are particular chemical groups or peptide sequences on a molecule that are antigenic, such that they elicit a specific immune response. An antibody binds a particular antigenic epitope, such as an epitope of on the surface of a pathogen.

Exogenous: A substance, such as an isolated opsonic antibody or complement protein of fragment thereof, that is obtained from a source other than the subject to which it is administered. For example, when an exogenous isolated opsonic antibody is administered to a subject according to the methods and compositions described herein, that isolated antibody is not obtained, for example isolated from the same subject to whom it is administered.

Fungal pathogen: A fungus that causes disease. Examples of fungal pathogens for which opsonophagocytosis can be enhanced in accordance with the disclosed methods include without limitation *Trichophyton rubrum*, *T. mentagrophytes*, *Epidermophyton floccosum*, *Microsporum canis*, *Pityrosporum orbiculare* (*Malassezia furfur*), *Candida* sp. (such as *Candida albicans*), *Aspergillus* sp. (such as *Aspergillus fumigatus*, *Aspergillus flavus* and *Aspergillus clavatus*), *Cryptococcus* sp. (such as *Cryptococcus neoformans*, *Cryptococcus gattii*, *Cryptococcus laurentii* and *Cryptococcus albidus*), *Histoplasma* sp. (such as *Histoplasma capsulatum*),

*Pneumocystis* sp. (such as *Pneumocystis jirovecii*), and *Stachybotrys* (such as *Stachybotrys chartarum*) among others.

Inhibiting or treating a disease: Inhibiting the full development of a disease or condition, for example, in a subject who is at risk for a disease such as an infection with a pathogen, for example a bacterial, fungal or viral pathogen. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component (such as a protein, for example P4 peptide, antibody or complement protein) has been substantially separated or purified away from other biological components in which the component naturally occurs, such as other chromosomal and extrachromosomal DNA, RNA, and proteins. Proteins or peptides that have been "isolated" include proteins purified by standard purification methods. The term also embraces proteins or peptides prepared by recombinant expression in a host cell as well as chemically synthesized proteins or peptides. Isolated does not require absolute purity, and can include protein or peptide molecules that are at least 50% isolated, such as at least 75%, 80%, 90%, 95%, 98%, 99%, or even 100% isolated.

Opsonin: A molecule that becomes attached to the surface of a pathogen, such as a bacterial, fungal or viral pathogen, that be recognized by surface receptors of neutrophils and macrophages and that increases the efficiency of phagocytosis of the microbe. Opsonins include IgG antibodies, which are recognized by the Fcγ receptor on phagocytes, and fragments of complement proteins, which are recognized by CR1 (CD35) and by the leukocyte integrin Mac-1.

Opsonophagocytosis: The process of attaching opsonins to microbial surfaces to target the microbes for phagocytosis by effector cells (such as macrophages and monocytes) in the presence of specific serum opsonins. Opsonins include any substance that binds to particulate antigens and induces their phagocytosis by effector cells. Exemplary opsonins include opsonizing antibodies (IgM, IgG1, IgG2, IgG3 and IgA immunoglobulins specific for the antigen) and certain complement fragments (C3a, C3b, iC3b, C3d, C4b, or C5a, which become bound to the antigen during complement activation), both of which trigger phagocytosis by binding to specific cell-surface receptors (such as Fc receptors and C3b receptors on neutrophils and macrophages, and C3d receptors on macrophages). In some examples, the activity of an effector cells for opsonophagocytosis of antibody/antigen complexes is enhanced by the presence of P4 peptides.

Peptide: Any compound composed of amino acids, amino acid analogs, chemically bound together. Peptide as used herein includes oligomers of amino acids, amino acid analog, or small and large peptides, including polypeptides or proteins. Any chain of amino acids, regardless of length or post-translational modification (such as glycosylation or phosphorylation). "Peptide" applies to amino acid polymers to naturally occurring amino acid polymers and non-naturally occurring amino acid polymer as well as in which one or more amino acid residue is a non-natural amino acid, for example an artificial chemical mimetic of a corresponding naturally occurring amino acid. In some embodiments, the peptide is a P4 peptide, which can include but is not limited to any of the modifications described herein. A "residue" refers to an amino acid or amino acid mimetic incorporated in a polypeptide by an amide bond or amide bond mimetic. A peptide has an amino terminal (N-terminal) end and a carboxy terminal (C-terminal) end. "Peptide" is used interchangeably with polypeptide or protein, and is used interchangeably herein to refer to a polymer of amino acid residues.

Amino acids generally are chemically bound together via amide linkages (CONH). Additionally, amino acids may be bound together by other chemical bonds. For example, linkages for amino acids or amino acid analogs can include $CH_2NH$—$CH_2S$—, —$CH_2$—$CH_2$—, —CH=CH— (cis and trans), —$COCH_2$—, $CH(OH)CH_2$—, and —$CHH_2SO$— (These and others can be found in Spatola, in Chemistry and Biochemistry of Amino Acids, Peptides, and Proteins, B. Weinstein, eds., Marcel Dekker, New York, p. 267 (1983); Spatula, A. F., Vega Data (March 1983), Vol. 1, Issue 3, Peptide Backbone Modifications (general review); Morley, Trends Pharm Sci pp. 463-468, 1980; Hudson, et al., *Int J Pept Prot Res* 14:177-185, 1979; Spatola et al. *Life Sci* 38:1243-1249, 1986; Harm *J. Chem. Soc Perkin Trans.* 1307-314, 1982; Almquist et al. *J. Med. Chem.* 23:1392-1398, 1980; Jennings-White et al. *Tetrahedron Lett* 23:2533, 1982; Holladay et al. *Tetrahedron. Lett* 24:4401-4404, 1983; and Hruby Life Sci 31:189-199, 1982.

Peptides may be modified by a variety of chemical techniques to produce derivatives having essentially the same activity as the unmodified proteins, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the protein, whether amino-terminal or side chain, may be in the form of a pharmaceutically-acceptable acid addition salt, such as the HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the protein side chains may be converted to $C_1$-$C_{16}$ alkoxy or to a $C_1$-$C_{16}$ ester using well-recognized techniques. Phenyl and phenolic rings of the protein side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the protein side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the proteins to select and provide conformational constraints to the structure that result in enhanced stability.

Pharmaceutically acceptable carriers: The pharmaceutically acceptable carriers of use with the disclosed methods are conventional carriers. *Remington's Pharmaceutical Sciences*, by E. W. Martin, Mack Publishing Co., Easton, Pa., 15th Edition, 1975, describes compositions and formulations suitable for pharmaceutical delivery of peptides and proteins, such as P4 peptides, opsonic antibodies and complement proteins, or fragments thereof.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol, or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical agent or drug: A chemical compound or composition capable of inducing a desired therapeutic or prophylactic effect when properly administered to a subject.

Serotype: The genotype of a unicellular organism, such as a bacterium, as defined by antisera against antigenic determinants expressed on the surface. Can also refer to the antigens themselves.

Specifically bind: When referring to an opsonin (such as an opsonic antibody), refers to a binding reaction which is determinative of the presence of a target protein, peptide, or polysaccharide in the presence of a heterogeneous population of proteins and other biologics. Thus, under designated conditions, an antibody binds preferentially to a particular target protein, peptide or polysaccharide (such as an antigen present on the surface of a pathogen, for example bacterial capsular polysaccharide) and do not bind in a significant amount to other proteins or polysaccharides present in the sample or subject.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a peptide sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer.

Therapeutically effective amount: A quantity of a specific substance (for example P4 peptide, opsonic antibody, antibiotic and/or complement protein) sufficient to achieve a desired effect in a subject being treated. For instance, this can be the amount necessary to inhibit or treat an infection by a pathogen, such as an infection by a bacterial pathogen. When administered to a subject, a dosage will generally be used that will achieve target tissue concentrations shown to achieve a desired in vitro effect.

A therapeutically effective amount of a substance, such as P4 peptide, opsonic antibody and/or complement protein can be administered in a single dose, or in several doses, for example daily, during a course of treatment. However, the effective amount of a composition will be dependent on the compound or peptide applied, the subject being treated, the severity and type of the affliction, and the manner of administration of the composition. For example, a therapeutically effective amount of composition can vary from about 0.01 mg/kg body weight to about 1 g/kg body weight.

Virus: A microscopic infectious organism that reproduces inside living cells. A virus consists essentially of a core of nucleic acid surrounded by a protein coat, and has the ability to replicate only inside a living cell. "Viral replication" is the production of additional virus by the occurrence of at least one viral life cycle. A virus may subvert the host cells' normal functions, causing the cell to behave in a manner determined by the virus. For example, a viral infection may result in a cell producing a cytokine, or responding to a cytokine, when the uninfected cell does not normally do so. In some examples, a virus is a pathogen. Specific examples of viral pathogens for which opsonophagocytosis can be enhanced in accordance with the disclosed methods include, without limitation; Arenaviruses (such as Guanarito virus, Lassa virus, Junin virus, Machupo virus and Sabia), Arteriviruses, Roniviruses, Astroviruses, Bunyaviruses (such as Crimean-Congo hemorrhagic fever virus and Hantavirus), Barnaviruses, Birnaviruses, Bornaviruses (such as Borna disease virus), Bromoviruses, Caliciviruses, Chrysoviruses, Coronaviruses (such as Coronavirus and SARS), Cystoviruses, Closteroviruses, Comoviruses, Dicistroviruses, Flaviruses (such as Yellow fever virus, West Nile virus, Hepatitis C virus, and Dengue fever virus), Filoviruses (such as Ebola virus and Marburg virus), Flexiviruses, Hepeviruses (such as Hepatitis E virus), human adenoviruses (such as human adenovirus A-F), human astroviruses, human BK polyomaviruses, human bocaviruses, human coronavirus (such as a human coronavirus HKU1, NL63, and OC43), human enteroviruses (such as human enterovirus A-D), human erythrovirus V9, human foamy viruses, human herpesviruses (such as human herpesvirus 1 (herpes simplex virus type 1), human herpesvirus 2 (herpes simplex virus type 2), human herpesvirus 3 (Varicella zoster virus), human herpesvirus 4 type 1 (Epstein-Barr virus type 1), human herpesvirus 4 type 2 (Epstein-Barr virus type 2), human herpesvirus 5 strain AD169, human herpesvirus 5 strain Merlin Strain, human herpesvirus 6A, human herpesvirus 6B, human herpesvirus 7, human herpesvirus 8 type M, human herpesvirus 8 type P and Human Cyotmegalovirus), human immunodeficiency viruses (HIV) (such as HIV 1 and HIV 2), human metapneumoviruses, human papillomaviruses (such as human papillomavirus-1, human papillomavirus-18, human papillomavirus-2, human papillomavirus-54, human papillomavirus-61, human papillomavirus-c and 90, human papillomavirus RTRX7, human papillomavirus type 10, human papillomavirus type 101, human papillomavirus type 103, human papillomavirus type 107, human papillomavirus type 16, human papillomavirus type 24, human papillomavirus type 26, human papillomavirus type 32, human papillomavirus type 34, human papillomavirus type 4, human papillomavirus type 41, human papillomavirus type 48, human papillomavirus type 49, human papillomavirus type 5, human papillomavirus type 50, human papillomavirus type 53, human papillomavirus type 60, human papillomavirus type 63, human papillomavirus type 6b, human papillomavirus type 7, human papillomavirus type 71, human papillomavirus type 9, human papillomavirus type 92, and human papillomavirus type 96), human parainfluenza viruses (such as human parainfluenza virus 1-3), human parechoviruses, human parvoviruses (such as human parvovirus 4 and human parvovirus B19), human respiratory syncytial viruses, human rhinoviruses (such as human rhinovirus A and human rhinovirus B), human spumaretroviruses, human T-lymphotropic viruses (such as human T-lymphotropic virus 1 and human T-lymphotropic virus 2), Human polyoma viruses, Hypoviruses, Leviviruses, Luteoviruses, Lymphocytic choriomeningitis viruses (LCM), Marnaviruses, Narnaviruses, Nidovirales, Nodaviruses, Orthomyxoviruses (such as Influenza viruses), Partitiviruses, Paramyxoviruses (such as Measles virus and Mumps virus), Picornaviruses (such as Poliovirus, the common cold virus, and Hepatitis A virus), Potyviruses, Poxviruses (such as Variola and Cowpox), Sequiviruses, Reoviruses (such as Rotavirus), Rhabdoviruses (such as Rabies virus), Rhabdoviruses (such as Vesicular stomatitis virus, Tetraviruses, Togaviruses (such as Rubella virus and Ross River virus), Tombusviruses, Totiviruses, Tymoviruses, Noroviruses, bovine herpesviruses including Bovine Herpesvirus (BHV) and malignant catarrhal fever virus (MCFV), among others. In some examples, a cell infected with a virus is opsonophagocytosed II. Overview of Several Embodiments This disclosure is related to methods of enhancing the opsonic response to pathogens and compositions for use in targeting a pathogen of interest for opsonophagocytosis. Opsonophagocytosis is the binding (or opsonization) of antibodies and complement or complement components to the pathogen and the subsequent uptake of the infectious agent by effector cells via the binding of the effector cells to the antibody/antigen complex.

During a protective immune response, functional antibodies are generated that bind to the infectious agents and also provide a means for uptake and clearance by effector cells. Functional antibodies (opsonic antibodies) that specifically bind an antigen on the surface of a pathogen of interest can be purified and administered to a subject to treat and/or inhibit an infection in the subject by targeting the pathogen of interest for opsonization by the subjects own effector cells. While such therapies appear promising, typically large doses of the opsonic antibody must be administered to reach the desired effect of pathogen clearance. Thus, the need exists for methods of enhancing the opsonic response for opsonic antibodies.

To meet this need, disclosed herein are methods of using P4 peptides to enhance the opsonic response to opsonic antibodies by effector cells when administered in conjunction with opsonic antibodies that target pathogens of interest by specifically binding antigen on their surface. The P4 peptides are derived from strand 7, α-helix 12, and strand 8 of the *Streptococcus pneumoniae* PsaA protein, but contain point mutations relative to the native sequence of the PsaA protein to increase the isoelectric point and enhance binding. The discovery that P4 peptides enhanced the opsonization of pathogens by effector cells, as disclosed herein, was particularly surprising and unexpected considering that the P4 peptides were initially developed to inhibit the internalization of *Streptococcus pneumoniae* by nasopharyngeal cells (see International Patent Publication WO 2006/127020). Furthermore, as disclosed herein, at has also been discovered that the coadministration of P4 peptide with antibiotics synergistically enhances the effectiveness of the antibiotics. Because of this synergistic behavior, it is possible to use lower doses of antibiotic when combined with P4 peptide, while still maintaining the effectiveness of the antibiotic.

A Methods of Treatment

Methods of enhancing opsonophagocytosis of a pathogen of interest in a subject are disclosed, for example to enhance the opsonophagocytosis of a pathogen of interest for the purpose of inhibiting and/or treating an infection in a subject from the pathogen of interest. The pathogen of interest can be any of the bacterial, viral or fungal pathogens discussed in the forgoing summary of terms. In particular examples the method is used to enhance the opsonophagocytosis in a subject who is infected with (or at risk of being infected with) a pathogen, (such as a viral, bacterial or fungal pathogen). In particular examples the pathogen is a bacterial pathogen, such as *Streptococcus* (such as *Streptococcus Pneumoniae*), *Staphylococcus* (such as *Staphylococcus aureus*), or *Meningococcus* (such as *Neisseria meningitides*). In some examples, a subject is selected for treatment that has or is at risk for developing an infection by a pathogen, (such as a viral, bacterial or fungal pathogen). In some examples, a subject is selected that has or is at risk of a *Streptococcus* infection (such as a *Streptococcus Pneumoniae* infection). In some examples, a subject is selected that has or is at risk of a *Staphylococcus* infection (such as a *Staphylococcus aureus* infection). In some examples, a subject is selected that has or is at risk of a *Meningococcus* infection (such as a *Neisseria meningitides* infection). In some examples a subject selected for treatment is not infected with a pathogen expressing Pneumococcal surface adhesin A (PsaA) protein, for example the selected subject is not infected with *Streptococcus Pneumoniae*. The methods include administering to the subject a therapeutically effective amount of isolated P4 peptide that includes an amino acid sequence that is at least 95% identical, such as at least 96% at least 97% at least 99% at least 99% identical or even 100% identical, to the amino acid sequence set forth as LFVESSVKRRPMKTVSQDTNIPIYAQIF (SEQ ID NO: 1), and optionally a therapeutically effective amount of one or more isolated opsonic antibodies or a fragment thereof that specifically bind an antigen present on the surface of the pathogen of interest (for example a bacterial, viral or fungal pathogen of interest listed above). In some examples a P4 peptide is between about 27 and about 200 amino acids in length, such as no more than 28, 29, 30, 40, 50, 60, 70, 80, 90, 100, 110, 120, 130, 140, 150, 160, 170, 180, 190, or 200 amino acids in length or even longer, for example 27-50, 40-60, 50-70, 60-80, 70-90, 80-100, 90-110, 100-120, 110-

130, 120-140, 130-140, 140-160, 150-170, 160-180, 170-190, or 180-200, amino acids in length. In some examples, a P4 peptide consists of the amino acid sequence set forth as SEQ ID NO: 1. In some examples, a subject is administered P4 peptide. In some examples, a subject is administered P4 peptide in conjunction with one or more isolated opsonic antibodies or a fragment thereof that specifically bind an antigen present on the surface of the pathogen of interest. In some examples, a subject is administered P4 peptide that has cells infected with a virus, for example to enhance the opsonophagocytosis of the cells expressing cell surface proteins from the viral pathogen of interest. In some examples, the P4 peptide includes an amino acid sequence that has no more than one or two amino acid changes from the amino acid sequence set forth as SEQ ID NO: 1, for example conservative substitutions. Changes in amino acid sequence can be utilized will still render the resultant peptide capable of enhancing opsonophagocytosis of a pathogen of interest are contemplated for example by conservative substitution. Also contemplated are fusion proteins that include a P4 peptide fused to a heterologous amino acid sequence. In some examples, the P4 peptide is lipidated, for example lipidated with a palmitic acid and the like. Exemplary pharmaceutical compositions are described below in section B. Various modes of administration of the pharmaceutical compositions of this disclosure are contemplated (see section B below).

The administration of the P4 peptide enhances the subject's ability (and specifically the ability of effector cells of the subject) to opsonophagocytose the pathogen of interest that is specifically bound by an opsonic antibody or fragment thereof, for example an opsonic antibody produced by the subject (for example a subject infected with a pathogen) and/or an isolated opsonic antibody administered to the subject. In some examples, an opsonic antibody or fragment thereof and the P4 peptide is administered to a subject. The administration of an opsonic antibody or fragment thereof and the P4 peptide can occur in any order or even simultaneously, for example by co-administration as a single pharmaceutical preparation, or as multiple preparations, such as a pharmaceutical composition that contains a therapeutically effective amount of P4 peptide and a composition that contains a therapeutically effective amount of an opsonic antibody or fragment thereof that specifically binds a pathogen of interest (or even multiple opsonic antibodies, for example multiple opsonic antibodies that each specifically bind a single pathogen of interest, or multiple opsonic antibodies where each opsonic antibody specifically binds a different pathogen of interest, or multiple serotypes of a single pathogen of interest, or any combination thereof) or even a composition that contains both a therapeutically effective amount of P4 peptide and a therapeutically effective amount of an opsonic antibody or fragment thereof (or multiple opsonic antibodies).

As disclosed herein the administration of the P4 peptide in conjunction with an antibiotic increases the effectiveness of the antibiotic, for example allowing a lower dose to be used and/or increasing bacterial clearance. In general any antibiotic can be used with the disclosed methods. Examples of antibiotics that can be used include but are not limited to aminoglycosides (such as amikacin, gentamicin, kanamycin, neomycin, netilmicin, streptomycin, tobramycin, and paromomycin); ansamycins (such as geldanamycin, and herbimycin); carbacephems (such as loracarbef, ertapenem, doripenem, imipenem/cilastatin, and meropenem); cephalosporins (such as cefadroxil, cefazolin, cefalotin, cefalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and ceftobiprole); glycopeptides (such as teicoplanin and vancomycin); macrolides (such as azithromycin, clarithromycin, dirithromycin, erythromycin, roxithromycin, troleandomycin, telithromycin, and spectinomycin); monobactams (such as aztreonam); penicillins (such as amoxicillin, ampicillin, azlocillin, carbenicillin, cloxacillin, dicloxacillin, flucloxacillin, mezlocillin, meticillin, nafcillin, oxacillin, penicillin, piperacillin, and ticarcillin); polypeptides (such as bacitracin, colistin, and polymyxin b); quinolones (such as ciprofloxacin, enoxacin, gatifloxacin, levofloxacin, lomefloxacin, moxifloxacin, norfloxacin, ofloxacin, trovafloxacin, grepafloxacin, and sparfloxacin); sulfonamides (such as mafenide, prontosil (archaic), sulfacetamide, sulfamethizole, sulfanilimide (archaic), sulfasalazine, sulfisoxazole, trimethoprim, and trimethoprim-sulfamethoxazole); tetracyclines (such as demeclocycline, doxycycline, minocycline, oxytetracycline, and tetracycline); and others (such as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampicin, thiamphenicol, and tinidazole). In some examples, an antibiotic (or more than one antibiotic) and the P4 peptide is administered to a subject. The administration of an antibiotic or fragment thereof and the P4 peptide can occur in any order or even simultaneously, for example by co-administration as a single pharmaceutical preparation, or as multiple preparations, such as a pharmaceutical composition that contains a therapeutically effective amount of P4 peptide and a composition that contains a therapeutically effective amount of an antibiotic that is specific for a pathogen of interest. In some examples, an opsonic antibody or fragment thereof, P4 peptide and antibiotic is administered to a subject. The administration of an opsonic antibody or fragment thereof, the P4 peptide and the antibiotic can occur in any order or even simultaneously, for example by co-administration as a single pharmaceutical preparation, or as multiple preparations, such as a pharmaceutical composition that contains a therapeutically effective amount of P4 peptide, a composition that contains a therapeutically effective amount of an antibiotic specific for a pathogen of interest, and a composition that contains a therapeutically effective amount of an opsonic antibody or fragment thereof that specifically binds a pathogen of interest (or even multiple opsonic antibodies, for example multiple opsonic antibodies that each specifically bind a single pathogen of interest, or multiple opsonic antibodies where each opsonic antibody specifically binds a different pathogen of interest, or multiple serotypes of a single pathogen of interest, or any combination thereof) or even a composition that contains a therapeutically effective amount of P4 peptide and a therapeutically effective amount of an opsonic antibody or fragment thereof (or multiple opsonic antibodies) and a therapeutically effective amount of an antibiotic specific for a pathogen of interest.

Complement proteins and fragments thereof assist in opsonophagocytosis of pathogens by binding to opsonic antibodies and facilitating the opsonization by effector cells. Thus, in some examples, the subject is also administered a pharmaceutically effective amount of an isolated complement protein or fragment thereof, such as one or more of C3a, C3b, iC3b, C3d, C4b, or C5a. In some examples a subject is selected that has a complement defect for administration of a pharmaceutically effective amount of an isolated complement protein or fragment thereof. In certain examples the therapeutically effective amount of the isolated P4 peptide is administered by an intranasal route and/or an intravenous route. In some embodiments, the therapeutically effective amount of the opsonic antibody or fragment thereof is administered by an intranasal route and/or an intravenous route. In some examples, the pharmaceutically effective amount of an isolated complement protein or a fragment thereof, such as one or more of C3a, C3b, iC3b, C3d, C4b, or C5a, is administered by an intranasal route and/or an intravenous route.

Because P4 peptides are not specific for any single pathogen, the P4 peptides and therapeutic compositions of this disclosure can be formulated to enhance the opsonophagocytosis of any pathogen of interest by providing an opsonic antibody or fragment thereof that targets any pathogen of interest, for example by providing an opsonic antibody or a fragment thereof (such as a therapeutically effective amount of an opsonic antibody or a fragment thereof) that specifically binds an antigen present on the surface of the pathogen of interest, or providing P4 peptide to a subject that is producing opsonic antibodies, for example a subject that is infected, or has been infected with a pathogen. Methods of producing opsonic antibodies are given below in section C. In some examples, the pathogen of interest is a bacterial pathogen and a therapeutically effective amount of an opsonic antibody that specifically binds the bacterial pathogen is provided. In certain examples, the pathogen of interest is *Streptococcus pneumoniae*. In other examples, the pathogen of interest is *Neisseria meningitides*. In still other examples, the pathogen of interest is *Staphylococcus aureus*, such as is methicillin resistant *Staphylococcus aureus* (MRSA). In some examples, the pathogen of interest is a viral pathogen and a therapeutically effective amount of an opsonic antibody that specifically binds the viral pathogen or a cell infected with the viral pathogen is provided. In some examples, the pathogen of interest is a fungal pathogen and a therapeutically effective amount of an opsonic antibody that specifically binds the fungal pathogen is provided.

B. Therapeutic Compositions

The P4 peptide can be administered in vitro, ex vivo or in vivo to a cell or subject. It is desirable to prepare P4 peptides as a pharmaceutical composition appropriate for the intended application, for example to inhibit or treat a pathogenic infection, such as an infection by a pathogen discussed in the foregoing summary of terms. Accordingly, methods for making a medicament or pharmaceutical composition containing a P4 peptide (and in some cases an opsonic antibody or a fragment thereof, antibiotic, and/or complement protein or a fragment thereof) are included herein. P4 peptides can be prepared for administration alone or with other active ingredients, such as antibiotics (for example the antibiotics described in Section A above) and/or other proteins, such as with an opsonic antibody, antibiotic (or even multiple antibiotics) and/or complement protein (or even multiple opsonic antibodies that are specific for different pathogens (cells infected with pathogens) and/or complement proteins, or fragments thereof). In some examples, a therapeutic composition includes P4 peptide. In some examples, a therapeutic composition includes an opsonic antibody. In some examples, a therapeutic composition includes an antibiotic. In some examples, a therapeutic composition includes an opsonic antibody and a P4 peptide. In some examples, a therapeutic composition includes an opsonic antibody, a P4 peptide and an antibiotic. In some examples, a therapeutic composition includes a complement protein or fragment thereof. In some examples, a therapeutic composition includes a complement protein or fragment thereof and a P4 peptide. In some examples, a therapeutic composition includes a complement protein or fragment thereof, an antibiotic and a P4 peptide. In some examples, a therapeutic composition includes a complement protein or fragment thereof, an opsonic antibody, an antibiotic and a P4 peptide. In some examples, a therapeutic composition includes a complement protein or fragment thereof and an opsonic antibody. When P4 peptide and opsonic antibody, and/or antibiotic and/or complement protein is administered to a subject, the administration can be concurrent or sequential. Sequential administration of the P4 peptide and opsonic antibody and/or antibiotic and/or complement protein can be separated by any amount of time so long as the administration of P4 peptide enhances the opsonic activity of the opsonic antibody. Multiple administrations of the compositions described herein are also contemplated.

In some embodiments, a disclosed therapeutic composition includes a therapeutically effective amount of isolated P4 peptide that includes an amino acid sequence that is at least 95% identical such as at least 96%, at least 97%, at least 98%, at least 99%, or even 100% identical to set forth as SEQ ID NO: 1 and optionally a therapeutically effective amount of one or more isolated opsonic antibodies or a fragment thereof that specifically binds to an antigen present on the surface of a pathogen of interest. In some examples, the therapeutic composition also includes a therapeutically effective amount of an antibiotic, or even more than one antibiotic. In some examples, the therapeutic composition also includes a therapeutically effective amount of an isolated complement protein or fragment thereof, such as one or more of C3a, C3b, iC3b, C3d, C4b, or C5a.

Typically, preparation of a pharmaceutical composition (for use as a medicament or in the manufacture of a medicament) entails preparing a pharmaceutical composition that is essentially free of pyrogens, as well as any other impurities that could be harmful to humans or animals. Typically, the pharmaceutical composition contains appropriate salts and buffers to render the components of the composition stable and allow the P4 peptide to interact with cells of a subject.

Administration of therapeutic compositions can be by any common route as long as the target tissue is available via that route. This includes oral, nasal (such as intranasal), ocular, buccal, enteral, intravitreal, or other mucosal (such as rectal or vaginal) or topical administration. Alternatively, administration will be by orthotopic, intradermal subcutaneous, intramuscular, parenteral, intraperitoneal, or intravenous injection routes. Such pharmaceutical compositions are usually administered as pharmaceutically acceptable compositions that include physiologically acceptable carriers, buffers or other excipients.

Therapeutic compositions can be provided as parenteral compositions, such as for injection or infusion. Such compositions are formulated generally by mixing P4 peptide at the desired degree of purity, in a unit dosage injectable form (solution, suspension, or emulsion), with a pharmaceutically acceptable carrier, for example one that is non-toxic to recipients at the dosages and concentrations employed and is compatible with other ingredients of the formulation. In addition, P4 peptides (and/or opsonic antibodies, and/or antibiotic, and/or complement protein or fragments thereof) can be suspended in an aqueous carrier, for example, in an isotonic buffer solution at a pH of about 3.0 to about 8.0, preferably at a pH of about 3.5 to about 7.4, 3.5 to 6.0, or 3.5 to about 5.0. Useful buffers include sodium citrate-citric acid and sodium phosphate-phosphoric acid, and sodium acetate/acetic acid buffers. The P4 peptide, optionally together with excipients, opsonic antibody, antibiotic and/or complement protein or fragments thereof, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount (such as a therapeutically effective amount) of P4 peptide, complement protein, antibiotic, and/or opsonic antibodies (for example, dissolved or suspended) in a pharmaceutically acceptable carrier or excipient. Pharmaceutically acceptable carriers and/or pharmaceutically acceptable excipients are known in the art and are described, for example, in *Remington's Pharmaceutical Sciences*, by E. W. Martin, Mack Publishing Co., Easton, Pa., 15th Edition (1975).

The nature of the carrier will depend on the particular mode of administration being employed. For example, parenteral formulations usually contain injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch or magnesium stearate. In addition, pharmaceutical compositions to be administered can contain minor amounts of non-toxic auxiliary substances, such as wetting or emulsifying agents, preservatives, and pH buffering agents and the like, for example sodium acetate or sorbitan monolaurate.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include P4 peptide in water, mixed with a suitable surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

Additional formulations are suitable for oral administration. Oral formulations can include excipients such as, pharmaceutical grades of mannitol, lactose, starch, magnesium stearate, sodium saccharine, cellulose, magnesium carbonate and the like. The compositions (medicaments) typically take the form of solutions, suspensions, aerosols or powders. Exemplary formulations can be found in U.S. Patent publication No. 20020031527. When the route is topical, the form may be a cream, ointment, salve or spray.

Typical subjects intended for treatment with the pharmaceutical compositions and methods of the present disclosure include humans, as well as non-human primates and other animals. To identify subjects for prophylaxis or treatment according to the methods of the disclosure, accepted screening methods are employed to determine risk factors associated with a targeted or suspected disease or condition (for example, an infection associated with a particular pathogen of interest) or to determine the status of an existing disease or condition in a subject. These screening methods include, for example, diagnostic methods, such as various ELISA and other immunoassay methods, which are available and well known in the art to detect and/or characterize disease-associated markers. These and other routine methods allow the clinician to select patients in need of therapy using the methods and pharmaceutical compositions of the disclosure.

An effective amount of the pharmaceutical composition is determined based on the intended goal, for example to inhibit and/or treat a pathogenic infection of a human or non-human subject. The administration of the pharmaceutical compositions of the disclosure can be for either prophylactic or therapeutic purpose. When provided prophylactically, the pharmaceutical composition is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the pharmaceutical compositions can be administered to the subject in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, porcine, feline, non-human primate, and other accepted animal model subjects known in the art. Alternatively, effective dosages can be determined using in vitro models (for example, immunologic and histopathologic assays). Using such models, only ordinary calculations and adjustments are required to determine an appropriate concentration and dose to administer a therapeutically effective amount of the P4 peptide (for example, amounts that are effective to alleviate one or more symptoms of a targeted infection).

The appropriate dose will vary depending on the characteristics of the subject, for example, whether the subject is a human or non-human, the age, weight, and other health considerations pertaining to the condition or status of the subject, the mode, route of administration, and number of doses, and whether the pharmaceutical composition includes both P4 peptide alone or in conjunction with an opsonic antibody and/or antibiotic and/or complement protein, time and route of administration, other drugs or treatments being administered concurrently, as well as the specific pharmacology of the therapeutic compositions for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a P4 peptide and/or other biologically active agent within the methods and formulations of the disclosure is about 0.01 mg/kg body weight to about 10 mg/kg body weight, such as about 0.05 mg/kg to about 5 mg/kg body weight, or about 0.2 mg/kg to about 2 mg/kg body weight.

Therapeutic compositions that include a disclosed therapeutic agent can be delivered by way of a pump (see Langer, supra; Sefton, *CRC Crit. Ref. Biomed. Eng.* 14:201, 1987; Buchwald et al., *Surgery* 88:507, 1980; Saudek et al., *N. Engl. J. Med.* 321:574, 1989) or by continuous subcutaneous infusions, for example, using a mini-pump. An intravenous bag solution can also be employed. One factor in selecting an appropriate dose is the result obtained, as measured by the methods disclosed here, as are deemed appropriate by the practitioner. Other controlled release systems are discussed in Langer (*Science* 249:1527-33, 1990).

In one example, a pump is implanted (for example see U.S. Pat. Nos. 6,436,091; 5,939,380; and 5,993,414). Implantable drug infusion devices are used to provide patients with a constant and long-term dosage or infusion of a therapeutic agent. Such device can be categorized as either active or passive.

Active drug or programmable infusion devices feature a pump or a metering system to deliver the agent into the patient's system. An example of such an active infusion device currently available is the Medtronic SYNCHROMED™ programmable pump. Passive infusion devices, in contrast, do not feature a pump, but rather rely upon a pressurized drug reservoir to deliver the agent of interest. An example of such a device includes the Medtronic ISOMED™.

In particular examples, therapeutic compositions including a disclosed therapeutic agent are administered by sustained-release systems. Suitable examples of sustained-release systems include suitable polymeric materials (such as, semipermeable polymer matrices in the form of shaped articles, for example films, or mirocapsules), suitable hydrophobic materials (for example as an emulsion in an acceptable oil) or ion exchange resins, and sparingly soluble derivatives (such as, for example, a sparingly soluble salt). Sustained-release compositions can be administered orally, parenterally, intracisternally, intraperitoneally, topically (as by powders, ointments, gels, drops or transdermal patch), or as an oral or nasal spray. Sustained-release matrices include polylactides (U.S. Pat. No. 3,773,919, EP 58,481), copolymers of L-glutamic acid and gamma-ethyl-L-glutamate (Sidman et al., *Biopolymers* 22:547-556, 1983), poly(2-hydroxyethyl methacrylate) (Langer et al., *J. Biomed. Mater. Res.* 15:167-277, 1981; Langer, *Chem. Tech.* 12:98-105, 1982), ethylene vinyl acetate (Langer et al., Id.) or poly-D-(–)-3-hydroxybutyric acid (EP 133,988).

Polymers can be used for ion-controlled release. Various degradable and nondegradable polymeric matrices for use in controlled drug delivery are known in the art (Langer, *Accounts Chem. Res.* 26:537, 1993). For example, the block copolymer, polaxamer 407 exists as a viscous yet mobile liquid at low temperatures but forms a semisolid gel at body temperature. It has shown to be an effective vehicle for formulation and sustained delivery of recombinant interleukin-2 and urease (Johnston et al., *Pharm. Res.* 9:425, 1992; and Pec, *J. Parent. Sci. Tech.* 44(2):58, 1990). Alternatively, hydroxyapatite has been used as a microcarrier for controlled release of proteins (Ijntema et al., *Int. J. Pharm.* 112:215, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa., 1993). Numerous additional systems for controlled delivery of therapeutic proteins are known (for example, U.S. Pat. No. 5,055,303; U.S. Pat. No. 5,188,837; U.S. Pat. No. 4,235,871; U.S. Pat. No. 4,501,728; U.S. Pat. No. 4,837,028; U.S. Pat. No. 4,957,735; and U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254,342; and U.S. Pat. No. 5,534,496).

The pharmaceutical compositions (medicaments) can be prepared for use in prophylactic regimens and administered to human or non-human subjects to protect against infection by a pathogen (or a plurality of pathogens). Thus, the pharmaceutical compositions typically contain a pharmaceutically effective amount of P4 peptide and optionally a pharmaceutically effective amount of opsonic antibody or a fragment thereof, and/or antibiotic and/or complement protein or a fragment thereof. In some cases the compositions are administered following infection, for example to treat the infection an increase pathogen clearance, in such applications, the pharmaceutical composition is administered in a therapeutically effective amount. A therapeutically effective amount is a quantity of a composition used to achieve a desired effect in a subject. For instance, this can be the amount of the composition necessary to inhibit infection by a pathogen, to increase pathogen clearance from the subject or to prevent or measurably alter outward symptoms of pathogen infection from a subject. When administered to a subject, a dosage will generally be used that will achieve target tissue concentrations that has been shown to achieve an in vitro or in vivo effect.

C. Opsonic Antibodies

An immunogen, such as an immunogenic polysaccharide or an immunogenic polypeptide (for example an immunogenic polysaccharide or an immunogenic peptide derived from a pathogen, such as a viral, bacterial, or fungal pathogen, for example the viral, bacterial, or fungal pathogens listed above) or a fragment or conservative variant thereof can be used to produce opsonic antibodies which are immunoreactive or bind to an epitope on the surface of a pathogen, for example bind to particulate antigens and induce the opsonophagocytosis of the target pathogen by effector cells. Polyclonal opsonic antibodies, antibodies which consist essentially of pooled opsonic monoclonal antibodies with different epitopic specificities, as well as distinct monoclonal opsonic antibody preparations are included.

The preparation of polyclonal antibodies is well-known to those skilled in the art. See, for example, Green et al., "Production of Polyclonal Antisera," in *Immunochemical Protocols* pages 1-5, Manson, ed., Humana Press 1992; Coligan et al., "Production of Polyclonal Antisera in Rabbits, Rats, Mice and Hamsters," in: *Current Protocols in Immunology*, section 2.4.1, 1992.

The preparation of monoclonal antibodies likewise is conventional. See, for example, Kohler & Milstein, *Nature* 256: 495, 1975; Coligan et al., sections 2.5.1-2.6.7; and Harlow et al., in: *Antibodies: a Laboratory Manual*, page 726, Cold Spring Harbor Pub., 1988. Briefly, monoclonal antibodies can be obtained by injecting mice with a composition comprising an antigen (for example an antigen derived from a pathogen), verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Methods of in vitro and in vivo multiplication of monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor, or in immobilized or entrapped cell culture. Multiplication in vivo may be carried out by injecting cell clones into mammals histocompatible with the parent cells, for example, syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from subhuman primate antibody. General techniques for raising therapeutically useful antibodies in baboons can be found, for example, in WO 91/11465, 1991, and Losman et al., Int. J. Cancer 46:310, 1990.

Alternatively, an antibody that specifically binds a polypeptide derived from a pathogen can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. U.S.A. 86:3833, 1989. Techniques for producing humanized monoclonal antibodies are described, for example, by Jones et al., Nature 321:522, 1986; Riechmann et al., Nature 332:323, 1988; Verhoeyen et al., Science 239:1534, 1988; Carter et al., Proc. Nat'l Acad. Sci. U.S.A. 89:4285, 1992; Sandhu, Crit. Rev. Biotech. 12:437, 1992; and Singer et al., J. Immunol. 150:2844, 1993.

Antibodies can be derived from human antibody fragments isolated from a combinatorial immunoglobulin library. See, for example, Barbas et al., in: Methods: a Companion to Methods in Enzymology, Vol. 2, page 119, 1991; Winter et al., Ann. Rev. Immunol. 12:433, 1994. Cloning and expression vectors that are useful for producing a human immunoglobulin phage library can be obtained, for example, from STRATAGENE® Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13, 1994; Lonberg et al., Nature 368:856, 1994; and Taylor et al., Int. Immunol. 6:579, 1994.

Antibodies include intact molecules as well as fragments thereof, such as Fab, F(ab')$_2$, and Fv which are capable of binding the epitopic determinant. Methods of making these fragments are known in the art. (See for example, Harlow and Lane, Antibodies: A Laboratory Manual, Cold Spring Harbor Laboratory, New York, 1988). An epitope is any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

Antibody fragments can be prepared by proteolytic hydrolysis of the antibody or by expression in E. coli of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., Arch. Biochem. Biophys. 89:230, 1960; Porter, Biochem. J. 73:119, 1959; Edelman et al., Methods in Enzymology, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

For example, Fv fragments comprise an association of $V_H$ and $V_L$ chains. This association may be noncovalent (Inbar et al., Proc. Nat'l Acad. Sci. U.S.A. 69:2659, 1972). Alternatively, the variable chains can be linked by an intermolecular disulfide bond or cross-linked by chemicals such as glutaraldehyde. See, for example, Sandhu, supra. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as E. coli. The recombinant host cells synthesize a single polypeptide chain with a linker peptide bridging the two V domains. Methods for producing sFvs are known in the art (see Whitlow et al., Methods: a Companion to Methods in Enzymology, Vol. 2, page 97, 1991; Bird et al., Science 242:423, 1988; U.S. Pat. No. 4,946,778; Pack et al., Bio/Technology 11:1271, 1993; and Sandhu, supra).

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., Methods: a Companion to Methods in Enzymology, Vol. 2, page 106, 1991).

Antibodies can be prepared using an intact polypeptide, fragments containing small peptides or polysaccharides of interest as the immunizing antigen. A polypeptide or a peptide used to immunize an animal can be derived from substantially purified polypeptide produced in host cells, in vitro translated cDNA, or chemical synthesis, which can be conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (for example, a mouse, a rat, or a rabbit).

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

It is also possible to use the anti-idiotype technology to produce monoclonal antibodies, which mimic an epitope. For example, an anti-idiotypic monoclonal antibody made to a first monoclonal antibody will have a binding domain in the hypervariable region that is the "image" of the epitope bound by the first monoclonal antibody.

Antibodies can be prepared by cloning techniques. Examples of appropriate cloning and sequencing techniques, and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987), or Ausubel et al. (eds.), *Current Protocols in Molecular Biology*, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® oratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.), and Applied Biosystems (Foster City, Calif.), as well as many other commercial sources known to one of skill.

A substantially pure target antigen derived from a pathogen suitable for use as an immunogen to produce opsonizing antibodies is isolated by purification or recombinant expression (see section D). Concentration of protein in the final preparation is adjusted, for example, by concentration on an Amicon filter device, to the level of a few micrograms per milliliter. Monoclonal or polyclonal antibody to the protein can then be prepared as described by Harlow and Lane (Antibodies, A Laboratory Manual, Cold Spring Harbor Press. 1988).

Alternatively, antibodies may be raised against a synthetic peptide synthesized on a commercially available peptide synthesizer based upon the predicted amino acid or known sequence of the target or internalizing receptor polypeptide (Harlow and Lane, Antibodies, A Laboratory Manual, Cold Spring Harbor Press. 1988).

Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, for example, Coligan et al., sections 2.7.1-2.7.12 and sections 2.9.1-2.9.3; Barnes et al., "Purification of Immunoglobulin G (IgG)," in: *Methods in Molecular Biology*, Vol. 10, pages 79-104, Humana Press, 1992.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan et al., Unit 9, *Current Protocols in Immunology*, Wiley Interscience, 1991).

To determine that a given antibody preparation (such as one produced in a mouse) specifically binds the target or internalizing receptor polypeptide of interest by Western blotting, total cellular protein containing the target or internalizing receptor polypeptide is extracted from murine myeloma cells and electrophoresed on a SDS-polyacrylamide gel. The proteins are then transferred to a membrane (for example, nitrocellulose), and the test antibody preparation is incubated with the membrane. After washing the membrane to remove non-specifically bound antibodies, the presence of specifically bound antibodies is detected by the use of an anti-mouse antibody conjugated to an enzyme such as alkaline phosphatase; application of the substrate 5-bromo-4-chloro-3-indolyl phosphate/nitro blue tetrazolium results in the production of a dense blue compound by immuno-localized alkaline phosphatase. Antibodies which specifically bind a target or internalizing receptor polypeptide of interest will, by this technique, be shown to bind to the target or internalizing receptor polypeptide band (which will be localized at a given position on the gel determined by its molecular weight). Non-specific binding of the antibody to other proteins (such as serum albumin) may occur and may be detectable as a weak signal on the Western blot. The non-specific nature of this binding will be recognized by one skilled in the art by the weak signal and/or unrelated portion obtained on the Western blot relative to the strong primary signal arising from the specific antibody-target or internalizing receptor polypeptide binding.

D. Peptide Production

The P4 peptides, complement peptides, and peptides derived from pathogens can be prepared by cloning techniques. Examples of appropriate cloning and sequencing techniques, and instructions sufficient to direct persons of skill through many cloning exercises are found in Sambrook et al., *Molecular Cloning: A Laboratory Manual* (2nd Ed.), Vols. 1-3, Cold Spring Harbor Laboratory (1989), Berger and Kimmel (eds.), *Guide to Molecular Cloning Techniques*, Academic Press, Inc., San Diego Calif. (1987), or Ausubel et al. (eds.), *Current Protocols in Molecular Biology*, Greene Publishing and Wiley-Interscience, NY (1987). Product information from manufacturers of biological reagents and experimental equipment also provide useful information. Such manufacturers include the SIGMA chemical company (Saint Louis, Mo.), R&D systems (Minneapolis, Minn.), Pharmacia LKB Biotechnology (Piscataway, N.J.), CLONTECH® laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), INVITROGEN™ (San Diego, Calif.), and Applied Biosystems (Foster City, Calif.), as well as many other commercial sources known to one of skill. In some examples, peptides, such as complement peptides are purified from a subject, for example from a blood fraction of a subject, such as serum obtained from a subject.

In some embodiments, the peptides are produced recombinantly, for example from cells transformed or transfected with polynucleotides encoding the peptides or portion thereof. Methods for the manipulation and insertion of the nucleic acids encoding the peptides of this disclosure or portions thereof into vectors for the expression of polypeptides are well known in the art (see for example, Sambrook et al., *Molecular Cloning, a Laboratory Manual*, 2d edition, Cold Spring Harbor Press, Cold Spring Harbor, N.Y., 1989, and Ausubel et al., *Current Protocols in Molecular Biology*, Greene Publishing Associates and John Wiley & Sons, New York, N.Y., 1994).

The nucleic acid constructs encoding the peptides or portions thereof of this disclosure can be inserted into plasmids. However, other vectors (for example, viral vectors, phage, cosmids, etc.) can be utilized to replicate the nucleic acids. In the context of this disclosure, the nucleic acid constructs typically are expression vectors that contain a promoter sequence which facilitates the efficient transcription of the inserted genetic sequence of the host. The expression vector typically contains an origin of replication, a promoter, as well as specific nucleic acid sequences that allow phenotypic selection of the transformed cells.

More generally, polynucleotide sequences encoding peptides or portions thereof of this disclosure can be operably linked to any promoter and/or enhancer that is capable of driving expression of the nucleic acid following introduction into a host cell. A promoter is an array of nucleic acid control sequences that directs transcription of a nucleic acid. Both constitutive and inducible promoters are included (see, for example, Bitter et al., *Methods in Enzymology* 153:516-544, 1987).

DNA sequences encoding peptides or portions thereof can be expressed in vitro by DNA transfer into a suitable host cell. The cell may be prokaryotic or eukaryotic. Hosts can include microbial, yeast, insect, and mammalian organisms. The term also includes any progeny of the subject host cell. Methods of stable transfer, meaning that the foreign DNA is continuously maintained in the host, are known in the art.

Transformation of a host cell with recombinant DNA can be carried out by conventional techniques that are well known to those of ordinary skill in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding peptides or portions thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). Peptides can then be purified for host cells using methods known in the art.

Immunogenic peptides derived from pathogens and/or P4 peptides also may be produced, for example by chemical synthesis by any of a number of manual or automated methods of synthesis known in the art. For example, solid phase peptide synthesis (SPPS) is carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/hydroxybenzotriazole or 2-(1H-benzo-triazol-1-yl)-1,1,3,3-tetramethyluronium hexafluorophosphate/hydroxybenzotriazole (HBTU/HOBT), and using p-hydroxymethylphenoxymethylpolystyrene (HMP) or Sasrin resin for carboxyl-terminus acids or Rink amide resin for carboxyl-terminus amides.

Fmoc-derivatized amino acids are prepared from the appropriate precursor amino acids by tritylation and triphenylmethanol in trifluoroacetic acid, followed by Fmoc derivitization as described by Atherton et al. Solid Phase Peptide Synthesis, IRL Press: Oxford, 1989.

Sasrin resin-bound peptides are cleaved using a solution of 1% TFA in dichloromethane to yield the protected peptide. Where appropriate, protected peptide precursors are cyclized between the amino- and carboxyl-termini by reaction of the amino-terminal free amine and carboxyl-terminal free acid using diphenylphosphorylazide in nascent peptides wherein the amino acid sidechains are protected.

HMP or Rink amide resin-bound products are routinely cleaved and protected sidechain-containing cyclized peptides deprotected using a solution comprised of trifluoroacetic acid (TFA), optionally also comprising water, thioanisole, and ethanedithiol, in ratios of 100:5:5:2.5, for 0.5-3 hours at room temperature.

Crude peptides are purified by preparative high pressure liquid chromatography (HPLC), for example using a Waters Delta-Pak C18 column and gradient elution with 0.1% TFA in water modified with acetonitrile. After column elution, acetonitrile is evaporated from the eluted fractions, which are then lyophilized. The identity of each product so produced and purified may be confirmed by fast atom bombardment mass spectroscopy (FABMS) or electrospray mass spectroscopy (ESMS).

Peptides produced by such methods can be used to produce opsonic antibodies for the pathogens from which the immunogenic peptides are derived. Methods of determining the opsonic ability of an antibody can be determined by methods, known to one of skill in the art, for example the methods described in International Patent Application No. PCT/US2006/015499 and U.S. patent application Ser. No. 11/910,517 which are incorporated herein by reference in their entirety.

The following examples are provided to illustrate particular features of certain embodiments. However, the particular features described below should not be construed as limitations on the scope of the disclosure, but rather as examples from which equivalents will be recognized by those of ordinary skill in the art.

EXAMPLES

Example 1

This example describes tests demonstrating enhancement of opsonophagocytosis by the P4 peptide.

Materials and Methods

Peptide Synthesis.

The amino acid sequences of the peptides designated P4, P6, and P7 have been described previously (see e.g. Rajam et al., *Microb Pathog* 2008; 44:186-96; Romero-Steiner et al., Vaccine 2006; 24:3224-31). The pure peptides with a free N- and C-terminus were synthesized and lyophilized at the Centers for Disease Control and Prevention (CDC) and the Emory University Microchemical Facility. Peptides used in this Example were synthesized in an Advanced ChemTech 396 multiple peptide synthesizer by means of standard and modified 9-fluorenylmethoxycarbonyl protocols. Lyophilized peptide was resuspended in diethylpyrocarbonate (DEPC) water, sonicated for 3 minutes for dissolution, and stored at −70° C. Two peptides, P6 and/or P7, were derived from the P4 sequence. These peptides had no activation effect on the eukaryotic cells tested (see Rajam et al., *Microb Pathog* 44:186-96, 2008). These peptides were used as negative controls in all in vitro tests described in this Example.

Species-Specific Antibodies Used in this Example.

Globulin (Gamunex®) has been used as a source of pneumococcal serotype-specific polysaccharide (Ps) antibodies (see e.g. Rajam et al., *Clin Vaccine Immunol*, 14:1223-7, 2007; Romero-Steiner et al., *Clin Diagn Lab Immunol* 10:1019-24, 2003). QC2, QC5, and QC268 are CDC in-house quality-control human sera with titers assigned to target organisms (see e.g. Martinez et al., *Clin Diagn Lab Immunol* 9:485-8, 2002; Martinez et al., *Clin Vaccine Immunol* 13:459-66, 2006). A monoclonal antibody with specificity for pneumococcal surface adhesin A as described by Srivastava et al. (*Hybridoma* 2000; 19:23-31), 8G12G11B10 (8G12), was also used as a source of anti-streptococcal protein antibody. These sera were selected to ensure the presence of specific antibodies and demonstrate the specificity of P4-mediated immune enhancement. The in vitro trial design involved direct comparison of changes in opsonophagocytic killing (OPK) or uptake in the presence or absence of P4.

OPK Assay.

In this Example, the reference OPK assay, as described in Romero-Steiner et al., *Clin Diagn Lab Immunol*, 4:415-22, 1997, was used with human promyelocytic leukemia cells (HL-60) differentiated into granulocytes. Gamma globulin was used as the source for serotype-specific antibodies for *S. pneumoniae* serotype 3 (WU2) was propagated, stored, and used in this assay as described by Romero-Steiner et al., *Clin Vaccine Immunol*, 13:165-9, 2006 and Rajam et al., *Clin Vaccine Immunol*, 14:1223-7, 2007. P4 peptide solution (100 μg/mL) was added to the OPK assay mixture at the preopsonization stage, and the control wells received 10 μL of DEPC water instead. P4-mediated enhancement of OPK was also assessed with *S. pneumoniae* serotypes 6B, 15B, 15C, and 19A, using gamma globulin or 8G12.

Flow Cytometric Opsonophagocytic Uptake Assay.

The flow cytometric opsonophagocytic assay (fOPA) was performed with HL-60 cells differentiated into granulocytes or monocytes as described by Martinez et al., *Clin Diagn Lab Immunol* 9:485-8, 2002; Martinez et al., *Clin Vaccine Immunol* 13:459-66, 2006; and Mezzatesta et al., *Infect Immun* 42:99-105, 1983. In-house quality-control sera (QC5 and QC268) were used as a source for serotypespecific antibodies against the capsular Ps of *S. pneumoniae* serotype 14 and *Neisseria meningitides* A, respectively. Polystyrene beads were covalently linked to *S. pneumoniae* and non-*S. pneumoniae* antigens, as described by Martinez et al., *Clin Diagn Lab Immunol* 9:485-8, 2002; and Martinez et al., *Clin Vaccine Immunol* 13:459-66, 2006 and used in fOPA. P4 peptide solution (100 μg/mL) was added to the fOPA mixture at the preopsonization stage, and the control wells received 10 μL of DEPC water instead.

OXYBURST® Labeling of *S. pneumoniae* Isolate.

To demonstrate the enhancement of the intracellular respiratory burst in the effector cells in response to P4-mediated activation, an OXYBURST®-labeled *S. pneumoniae* isolate was used. A loopful of the frozen stock of *S. pneumoniae* serotype 23F was grown overnight (37° C. in 5% $CO_2$) in Todd-Hewitt broth (Difco) supplemented with 0.5% yeast extract (THYE). A loopful of the overnight culture was transferred to 1 mL of fresh THYE broth and incubated for 3 hours. From this, 200 μL was transferred to 5 mL of THYE broth and incubated for 3 hours, after which 1 mL was transferred to 5 mL of THYE broth and incubated for another 3 hours (all incubations were done at 37° C. in 5% $CO_2$). After the third passage, the bacterial suspension was centrifuged at 6000 g for 10 minutes and resuspended in 1 mL of 0.01 mol/L phosphate buffered saline (PBS). OXYBURST® stain (INVITROGEN®) was reconstituted with 1 mL of deionized water, and 50 μL was added to the 1-mL bacterial suspension. This was allowed to mix thoroughly in a rotary shaker overnight at 4° C. After that, the OXYBURST®-labeled bacterial suspension was washed twice in PBS and used as a source of antigen instead of polystyrene beads in fOPA. In-house quality-control serum (QC2) was used in this assay.

Isolation of Polymorphonuclear Leukocytes from Human Blood.

Heparinized venous blood was obtained from the Emory Blood Donor Services. A leukocyte separation kit, HISTOPAQUE®-1119 (Sigma), was used to separate granulocytes from the blood, in accordance with the method recommended by the manufacturer.

Mouse strains. Mice (*Mus musculus*) of strain Swiss Webster (ND4-SW) were obtained from Charles River Laboratories. Mice used in this study were 6-10 weeks old. All experiments were approved by the institutional committee and were conducted according to institutional ethical guidelines for animal experiments and safety guidelines.

Bacterial Strains.

*S. pneumoniae* WU2 (serotype 3) was used for mouse infections. This *S. pneumoniae* isolate was selected from the Streptococcal Reference Laboratory, CDC. Briefly, *S. pneumoniae* isolate (frozen stock) was streaked on a blood agar plate (blood agar base plus 5% sheep blood) and incubated (at 37° C. in 5% $CO^2$) for 18-24 hours. *S. pneumoniae* colonies on blood agar plates were scraped with an inoculation loop and grown in 5 mL of THYE broth for ~4 hours (at 37° C. in 5% $CO^2$) until midlog phase (optical density read at 492 nm, 0.5-0.6). This culture (1.5 mL) was centrifuged in a 2-mL polypropylene screw-cap tube at 10,000 g for 5 minutes, and the wet pellet was resuspended in 1 mL of 0.1 mol/L PBS (pH 7.2). The 1-mL bacterial suspension was placed on ice and used for infections. It was also diluted $10^{-6}$ with PBS, and the viable bacterial load was enumerated on blood agar plates. The average viable bacterial load was $4 \times 10^7$ cells/mL.

Intranasal Infection.

Mice were intranasally infected with *S. pneumoniae* by means of methods described by Briles et al., *J Infect Dis* 188:339-48, 2003. Briefly, a mouse was injected intraperitoneally with 20 μL of KETASET® (100 mg/mL ketamine hydrochloride; Wyeth). Once the mouse was lethargic, 40 μL of the previously prepared bacterial suspension was dispensed drop by drop close to the nose, allowing the mouse to inhale the infection.

Intraperitoneal (ip) and Intravenous (iv) Therapy.

Infection with $4 \times 10^7$ cells of *S. pneumoniae* WU2 per mouse resulted in moribund characteristics at 48 hours in 50%-60% of animals. At 72 hours, all the infected mice were moribund (n=60; moribund score, 2-3 [see below]). At 72 and 96 hours after infection, 40 animals were passively immunized with gamma globulin (100 μL/mouse; iv, n=20; ip, n=20). After a time lapse of 20 minutes, allowing for possible preopsonization in vivo, 20 of the passively immunized mice (intravenous (iv), n=10; intraperitoneal (ip), n=10) received P4 (100 µg; 100 µL/mouse) through an iv or ip route. Control mice were given DEPC water (100 µL) or P4 alone. Initially, P4 peptide was tested for toxicity in mice at 1, 10, 100, and 1000 µg. P4 was injected ip into 10-week-old ND4-SW mice at a constant volume of 100 µL. P4 had no apparent toxic effect on mice, even at doses of 1000 µg/mouse.

Scoring of Moribund Characteristics.

Mice were monitored and visually scored twice daily for moribund characteristics. Mice were ranked on a scale of 5 to 0, in which 5 indicated healthy with normal coat, skin, eyes, breathing, and activity/movement; 4, healthy but beginning to look sick, ruffled coat; 3, sick, ruffled coat, decreased activity; 2, very sick, ruffled coat, decreased activity, eye secretions; 1, near death, ruffled coat, little or no activity, eye secretions, decreased breathing (these animals were, hence, euthanized); and 0, dead.

Cytokine Analysis.

P4-treated and control mice were killed and decapitated. The blood was quickly collected in cryovials from the base of the neck and allowed to stand at 4° C. for 30 minutes. The tube was then centrifuged at 1000 g for 10 minutes. Serum samples were collected and used immediately for cytokine analysis. Cytokines were analyzed in mouse serum by means of the LUMINEX®-based LINCOPLEX™ mouse 22-plex cytokine kit (MCYTO-70K-PMX22; LINCO Research), using the manufacturer-recommended protocol.

Statistics.

All in vitro experiments were performed in triplicate on 3 separate assay days, unless specified otherwise. The in vivo challenge experiments were repeated >5 times. The number of moribund animals after treatment was recorded for 166 hours, and the data were analyzed for significant differences among various groups by use of at test with paired samples for means (Microsoft® Excel 2003).

Results

OPK Assay.

Figure 1B:
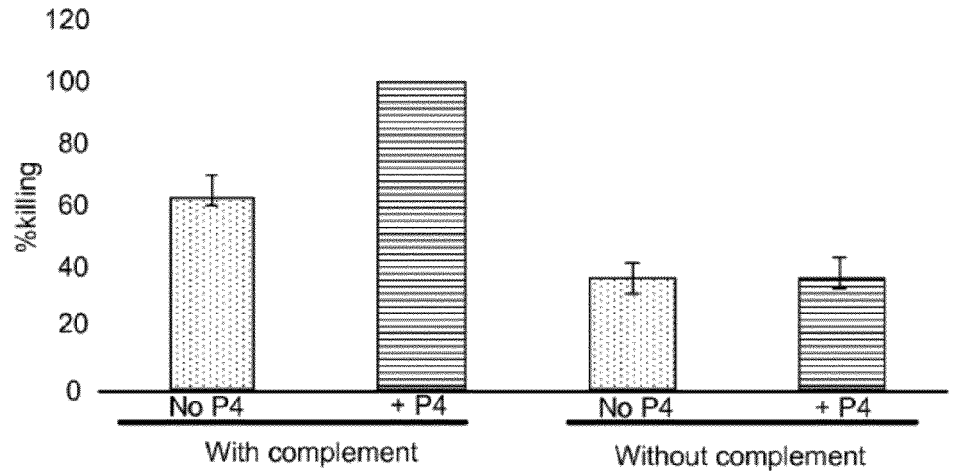
Figure 1C:
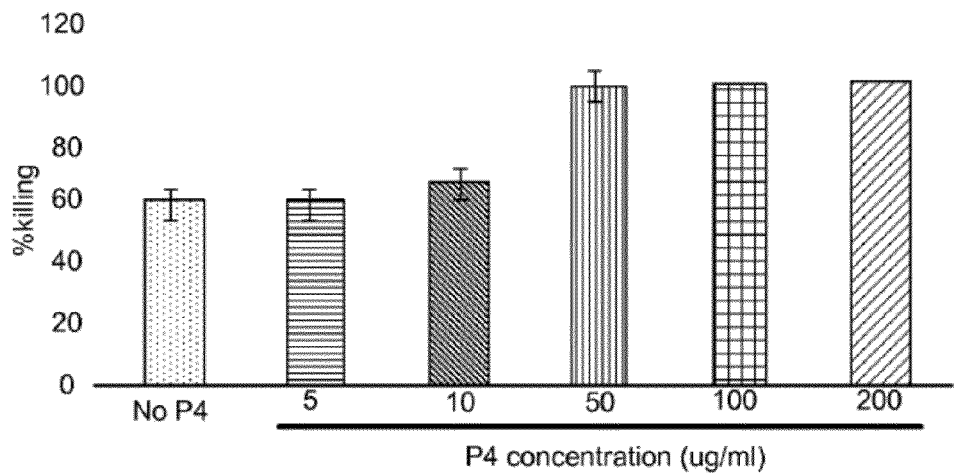

P4 peptide was tested for its potential to enhance opsonophagocytosis in vitro, and the data are given in FIG. 1. Data presented in FIG. 1A show that the P4-mediated increase in OPK of S. pneumoniae serotype 3 (WU2) was dependent on the antibody concentration. Although a 35% increase in OPK is seen at a 1:8 dilution of gamma globulin, the effect titrates out with the dilution of the antiserum (FIG. 1A). The P4-mediated increase in OPK was complement dependent, because no increase in OPK with P4 over control was observed in the absence of a complement source (FIG. 1B). The P4-mediated enhancement of OPK was dependent on the concentration of P4 in the reaction mixture. Although no change in OPK was seen with P4 supplementation at 5 µg/mL, a gradual increase was seen with an increase in P4 concentration (for 10 µg/mL, 8%; for 50 µg/mL, 30%; for 100 µg/mL, 35%). At a concentration of 100 µg/mL, the P4-mediated increase in OPK plateaued (FIG. 1C). A similar P4-mediated increase in OPK was also recorded with S. pneumoniae serotypes 6B, 15B, 15C, and 19A, using gamma globulin or 8G12 as the source of specific antibodies.

Opsonophagocytic Uptake (OPU) Assay.

P4-mediated enhancement of opsonophagocytosis was tested for changes in the intraphagocytic respiratory burst by means of OXYBURST® labeled S. pneumoniae serotype 23F (DS3848-03). P4-mediated increase in OPU was characterized by an increase in the intraphagocytic respiratory burst that titrated out with the antibody dilution (FIG. 2A). Data presented in FIGS. 2B and 2C show P4 as being pluripotent in activating different effector cells and enhancing OPU in the presence of antigen-specific antibodies and complement. There was a 50% increase in OPU of S. pneumoniae serotype 14 Ps beads by the granulocytes isolated from fresh human blood, which titrated out with the antibody dilution (for 1:64, 52%; for 1:128, 48%; for 1:256, 25%; for 1:512, 5%) (FIG. 2B). FIG. 2C shows that P4 can enhance in vitro opsonophagocytosis of non-S. pneumoniae antigens in the presence of specific antibodies and effector cells. A P4-mediated increase in the OPU of beads coated with N. meningitidis APs was recorded, with HL-60 cells differentiated into monocytes (FIG. 2C).

In Vivo Studies.

Figure 3:
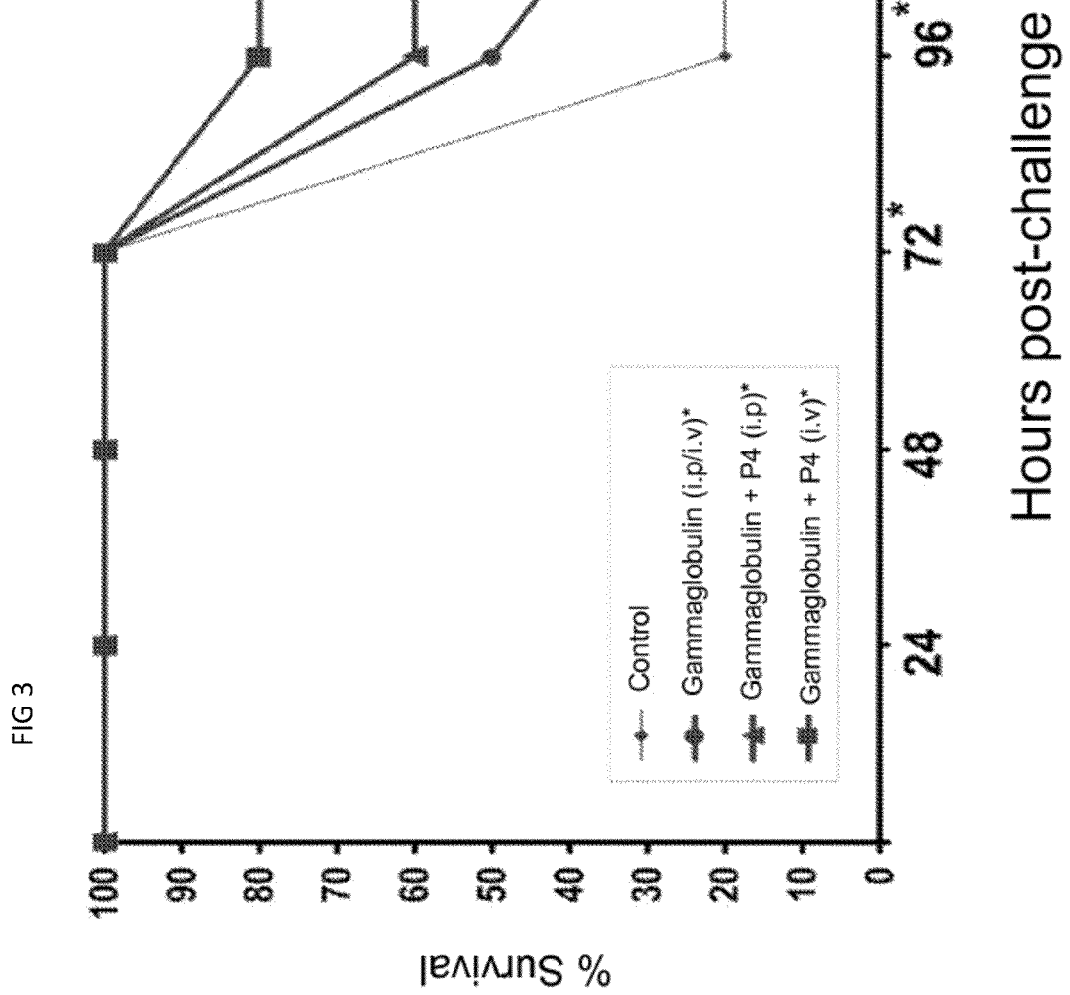
FIG. 3 is a graph demonstrating the conferral of protection against lethal intranasal Streptococcus pneumoniae serotype 3 (WU2) challenge by P4 with serotype-specific IgG. Intravenous (iv) injection of P4 (100 µg/mouse) with gamma globulin (100 µL/mouse) at 72 and 96 hours after challenge provided highly significant protection (80%; P<0.001) against lethal S. pneumoniae WU2 infection, followed in effectiveness by the intraperitoneal (ip) route of administration (60%; P<0.001).

Mice infected with S. pneumoniae WU2 were passively immunized with gamma globulin and/or P4 at 72 and 96 hours after infection. Although the untreated mice had 10% survival (1 in 10), mice treated with gamma globulin alone (both iv and ip) had 30% survival. On the other hand, 8 (80%) of 10 mice (P<0.001) treated with iv and 6 (60%) of 10 mice (P<0.001) treated with ip gamma globulin and P4 exhibited complete remission of bacteremia and moribundity (FIG. 3). Cytokine analysis of mouse serum samples showed no consistent pattern or changes in cytokine levels in the rescued animals.

Example 2

This example describes the evaluation of co-administration of P4 peptide and antibiotics as a novel therapeutic approach to treating severe pneumococcal infection.

Materials and Methods

Bacterium, Peptide, Antibodies, and Antibiotic Used in this Example.

S. pneumoniae serotype 3 (WU2) was used for mouse infections as described previously (Rajam et al. *J. Infect. Dis.* 199:1233-1238, 1999). P4, a 28-amino-acid peptide, was synthesized, purified, and prepared for combination therapy as described previously (Carlone et al. *Microb. Pathog.* 44:186-196, 2008). Gamma globulin (intravenous immunoglobulin [IVIG]; Gamunex, Telecris, N.C.) was used as a source of Pnc serotype-specific polysaccharide antibodies (Frasch and Scott *Clin. Diagn. Lab. Immunol.* 11:1158-1164, 2004; Rajam et al., *Clin. Vaccine Immunol.* 14:1223-1227, 2007; Romero-Steiner et al., *Clin. Diagn. Lab. Immunol.* 10:1019-1024, 2003). Ceftriaxone (catalog no. C5793; Sigma-Aldrich, St. Louis, Mo.), an expanded-spectrum cephalosporin, was dissolved in phosphate-buffered saline (0.01 M), and working dilutions in phosphate-buffered saline were made for mouse inoculations.

Mice Used in this Example.

Female Swiss Webster mice (Charles River Laboratories, Wilmington, Mass.) 6 to 10 weeks of age were used in this study. All experiments were approved by the Institutional Animal Care and Use Committee (IACUC) and conducted according to the institutional ethical guidelines for animal experiments and safety guidelines.

Intranasal Infection.

Intranasal infections of mice with a Pnc isolate were carried out by adopting the methodology described by Briles et al., 2003. Briefly, a mouse was injected intraperitoneally (ip) with 20 µl of 100-mg/ml ketamine hydrochloride (KETASET®; Wyeth). Once the mouse was lethargic, 40 µl of the bacterial suspension (~2.1×10$^7$ cells/mouse) was dispensed drop by drop close to the nose, allowing the mouse to inhale the bacteria. Scruffiness combined with a hunched posture or lethargy indicated moribundity in a mouse. Most mice (80%) were moribund at 48 hours postexposure. Moribund mice were divided into various control and treatment groups (n=10/group) as shown in Table 1. Control groups included untreated animals or animals that received P4 alone, IVIG alone, or ceftriaxone (at 0.3, 3.0, 300, or 3,000 μg/mouse) alone. Treatment groups included mice that received a single inoculum containing P4 and IVIG with or without ceftriaxone at one of three different doses (0.3, 3.0, or 300 μg/mouse).

Combination Therapy.

Mice were restrained using a Tailveiner restrainer (model no. TV-150; Braintree Scientific, Braintree, Mass.). IVIG and/or P4 was administered intravenously (iv) using a 25-gauge needle and a 1-ml syringe. IVIG (100-μl volume/mouse) was administered first, followed 20 min later by P4 (50 μg in a 100-μl volume/mouse). Ceftriaxone was administered (ip in a 100-μl volume/mouse) 30 min after P4 administration. Animals were monitored daily for 7 days or (in the repeat infection study) 36 days post treatment for clinical signs of disease progression. For repeat therapy, mice rescued with P4 combination therapy were reinfected on day 28 post treatment and treated again with P4 combination therapy. Even though 25 to 30% of mice in the control group survived the first challenge, they later either succumbed to infection or were terminally ill and hence were humanely euthanized. Hence, there were no control mice from the first challenge for the repeat therapy.

Test for Bacteremia.

Blood samples from P4-treated and untreated mice were collected (Rajam et al., *J. Infect. Dis.* 199:1233-1238, 2009), and 100-0 aliquots of the heparinized blood samples were spread onto plates of blood agar (blood agar base plus 5% sheep blood plus gentamicin [2.5 mg/liter]). The plates were incubated for 18 to 24 hours at 37° C. in 5% $CO^2$, and bacteria were counted.

P4-Enhanced Opsonophagocytosis.

We used the in vitro opsonophagocytic killing assay (OPKA) as described previously by Romero-Steiner et al. (Romero-Steiner et al., *Clin. Diagn. Lab. Immunol.* 4:415-422, 1997) with polymorphonuclear leukocytes (PMNs) isolated from mice (Devi et al., *Indian J. Physiol. Pharmacol.* 39:354-360, 1995). Peripheral blood samples were collected from mice 1 and 2 hours postinfection (with Pnc WU2) or from uninfected controls as described previously (Frasch and Scott, 2004), and the buffy coat fractions were separated (Devi et al, 1995) and used as the source of effector cells. Gamma globulin (Gamunex, Telecris, N.C.) was used as the serotype-specific antibody source. *S. pneumoniae* serotype 3 (WU2) was propagated, stored, and used in this assay as described previously (Rajam et al., 2007; Romero-Steiner, 2006). A 100-μg/ml P4 peptide solution was added to the OPKA mixture at the preopsonization stage, and the control wells received diethyl pyrocarbonate water.

ELISA for Anti-P4 IgG.

Blood samples from mice treated with P4 therapy were collected 14 days post infection, and the serum fractions were separated by adopting the methodology described previously (Rajam, 2009). An enzyme-linked immunosorbent assay (ELISA) was performed to detect and quantify antiprotein immunoglobulin G (IgG) as described previously, with minor modifications (Scott, et al., *Clin. Diagn. Lab. Immunol.* 12:1195-1201, 2005; Scott et al., *J. Infect. Dis.* 186:220-226, 2002). Briefly, ELISA plates were coated with the P4 peptide at a 5-μg/ml concentration. Plates were incubated at 4° C. overnight and used to detect and quantify anti-P4 IgG in mouse sera. Horseradish peroxidase-labeled anti-mouse IgG (Sigma, St. Louis, Mo.) was used as the reporter antibody. SUREBLUE® 3,3',5,5'-tetramethylbenzidine (KPL, Gaithersburg, Md.) was used as the substrate, and 1 N HCl was used as the stop solution. Samples were assayed in triplicate, and suitable positive and negative controls were included.

Statistics.

The in vivo combination therapy experiments were repeated three to five times, and repeat therapy was performed once. The numbers of moribund animals up to 7 and 36 days after the combination and repeat therapies, respectively, were recorded, and the data were analyzed for significant differences among various groups by using the paired two-sample t test for means in MICROSOFT® Excel 2003.

Results

Combination Therapy.

Figure 4:
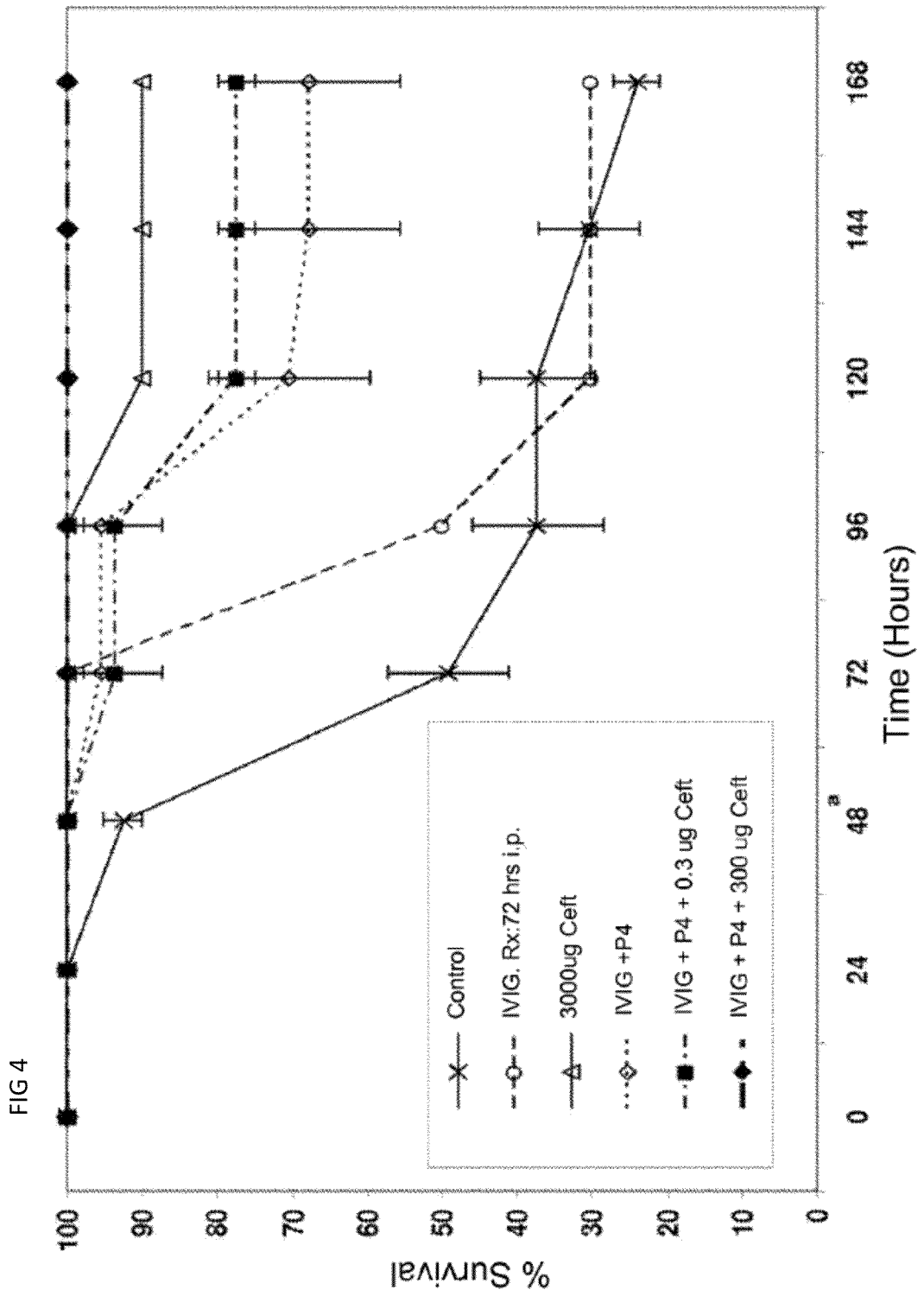
FIG. 4 is a graph demonstrating the survival of mice in various treatment arms and of control mice following exposure to S. pneumoniae serotype 3 (WU2). A single-dose iv injection of a mixture of P4 and gamma globulin (WIG) with ip injection of ceftriaxone (Ceft) provided highly significant protection (100%; P<0.05) compared to that of untreated controls.

Untreated control mice (n=10) had a 30% survival rate at 168 hours. Mice treated with ceftriaxone alone at 3,000 μg had a 90% survival rate (FIG. 4). On the other hand, ceftriaxone at lower doses (300, 3.0, and 0.3 μg) or P4 alone offered poor protection, with survival rates comparable to that of untreated controls. Treating moribund mice with a P4 concentration of 50 μg with IVIG administered in a single dose led to a survival rate of 70% (FIG. 4). Combining a low dose (300 μg) of ceftriaxone with this IVIG-P4 therapeutic mixture increased the mouse survival rate to 100%, significantly better than that of untreated controls (P<0.05) (FIG. 4).

Repeat Therapy.

Figure 5:
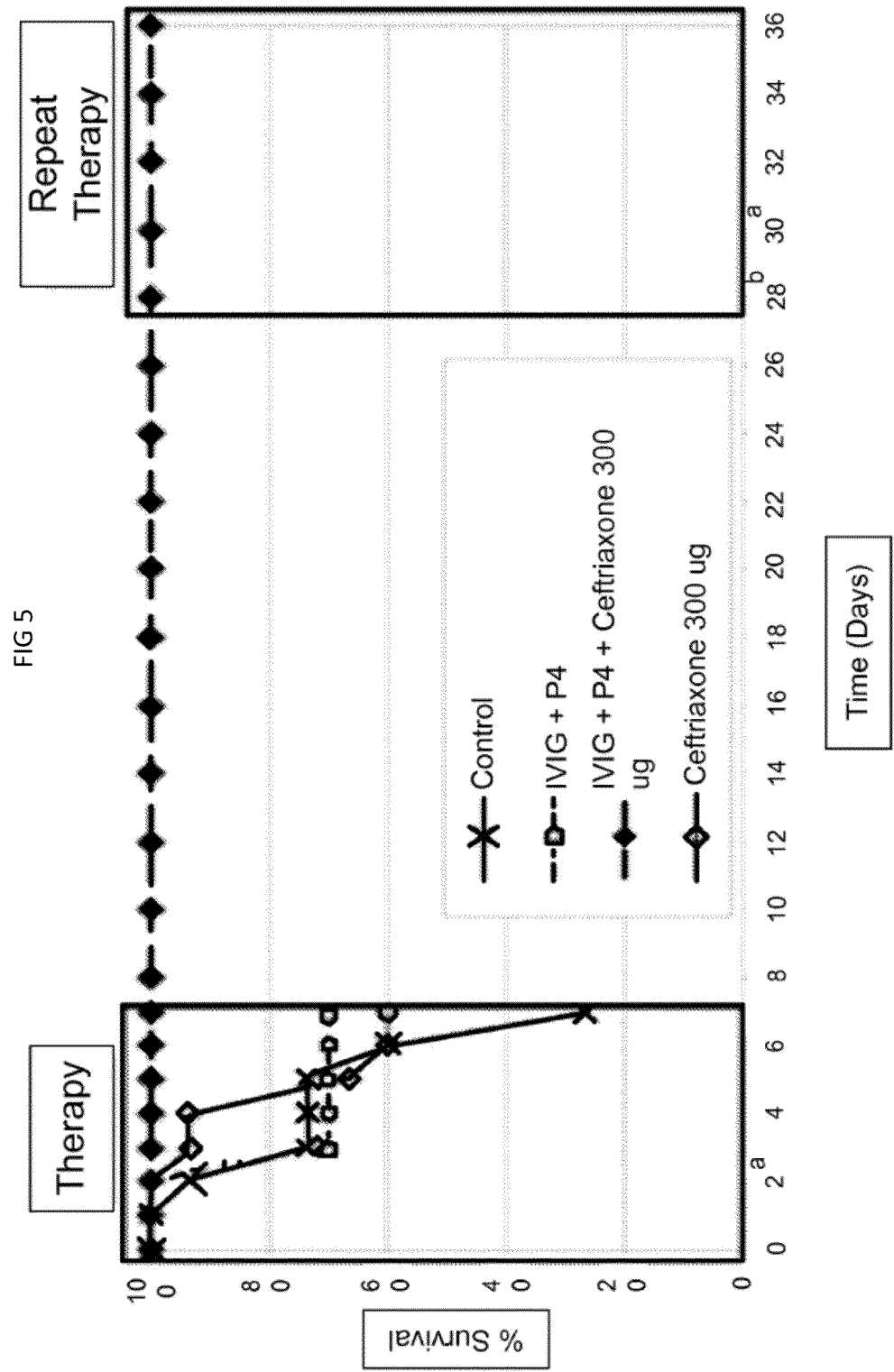
FIG. 5 is a graph showing the effects on mice previously rescued (♦) with P4 combination therapy that were reinfected with S. pneumoniae serotype 3(WU2) on day 28. A single dose of P4, gamma globulin (IVIG), and ceftriaxone was administered 2 days later. All animals (100%) were protected.

Mice (n=10) rescued from fatal *S. pneumoniae* WU2 infection with combination (P4, WIG, and ceftriaxone) therapy were reinfected with *S. pneumoniae* WU2 after 28 days and retreated with the combination therapy when they appeared to be moribund. P4-mediated combination therapy rescued all the infected animals (FIG. 5).

Test for Bacteremia.

Blood samples from P4-treated and untreated mice were drawn and tested for bacteremia. Blood samples from the untreated control mice contained loads of bacteria too numerous to count. Samples from treated animals had no bacteremia.

P4-Enhanced Opsonophagocytosis.

Figure 6:
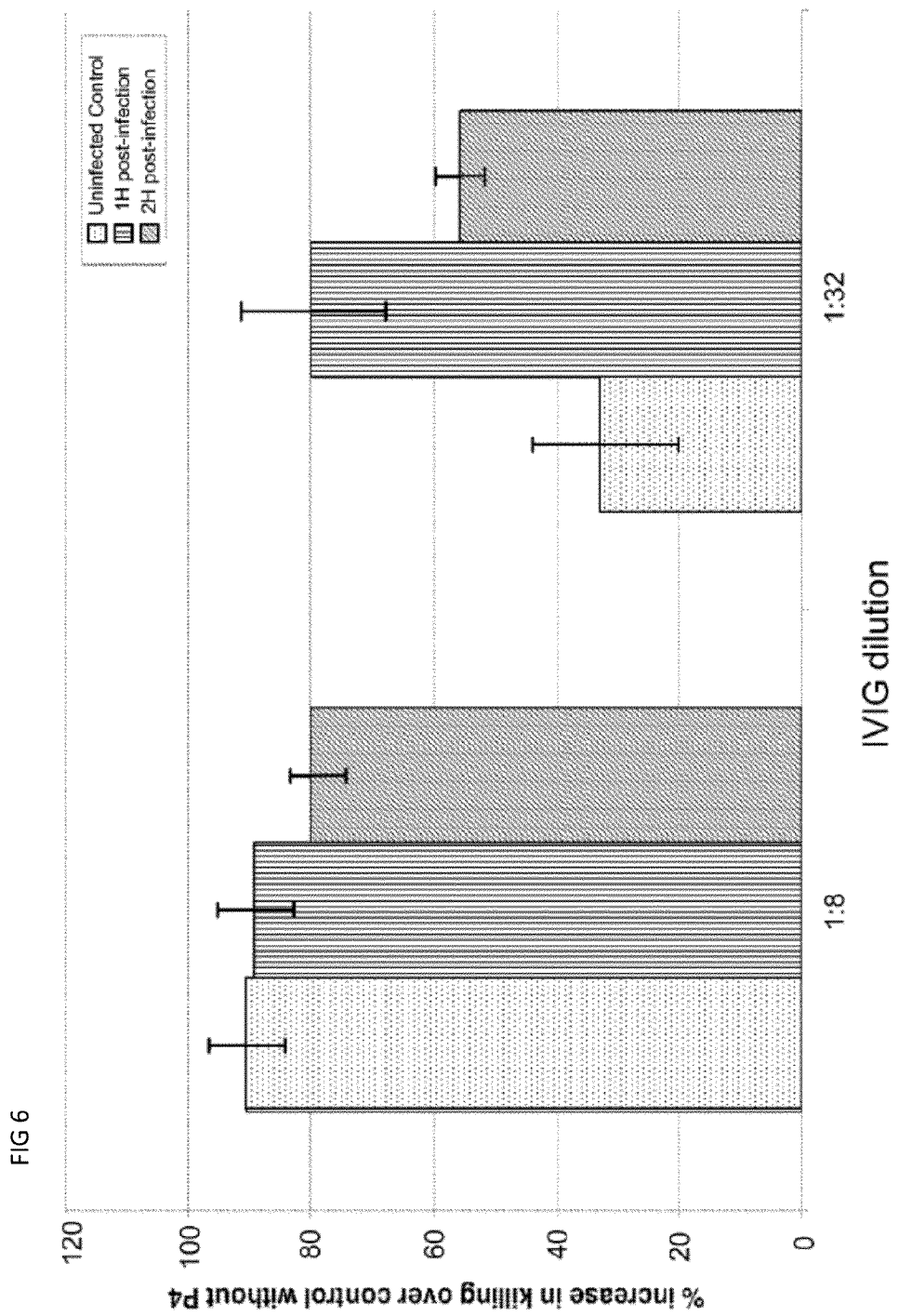
FIG. 6 is a set of bar graphs showing the results of an in vitro opsonophagocytotic killing assay (OPKA) assay with peripheral blood PMNs isolated from mice 1 and 2 hours postinfection or from uninfected mice. Gamma globulin (IVIG) was used as the source for serotype-specific antibodies. The addition of P4 increased the opsonophagocytic killing of S. pneumoniae serotype 3 (WU2) by 80% over that by PMNs from control mice not receiving P4 (P<0.05).

An OPKA with PMNs from either infected or uninfected mice was performed. The addition of P4 significantly increased (by >80%; P<0.05) the in vitro opsonophagocytic killing of Pnc (WU2) over the control level in the presence of serotype-specific IgG (FIG. 6).

ELISA for Anti-P4 IgG.

Serum samples from P4-treated mice were tested for anti-P4 by using a mouse IgG-specific ELISA. All the samples were negative for anti-P4 IgG.

TABLE 1

Study design

| | | | | Use[b] of: | | | |
|---|---|---|---|---|---|---|---|
| | | | | | Ceftriaxone | | |
| Treatment | Group[a] | P4 | Gamma globulin | 3,000 μg | 300 μg | 3.0 μg | 0.3 μg |
| Combination therapy | 1 | − | − | − | − | − | − |
| | 2 | + | − | − | − | − | − |
| | 3 | − | + | − | − | − | − |
| | 4 | − | − | + | − | − | − |
| | 5 | − | − | − | + | − | − |
| | 6 | − | − | − | − | + | − |
| | 7 | − | − | − | − | − | + |
| | 8 | + | + | − | − | − | − |
| | 9 | + | + | − | + | − | − |
| | 10 | + | + | − | − | + | − |
| | 11 | + | + | − | − | − | + |
| Repeat therapy | 10 | + | + | − | − | + | − |

[a] n = 10/group. All groups received *S. pneumoniae* serotype 3 (WU2) intranasally at ~2.1 × $10^7$ cells/40 μl/mouse.
[b] P4 at 50 μg in a 100-μl volume and 100 μl of gamma globulin were administered iv; ceftriaxone was administered ip at the indicated doses in a 100-μl volume.
+, included in the therapeutic mixture;
−, not included in the therapeutic mixture.

Example 3

Treatment of Subjects with P4 Peptide

This example describes methods that can be used to treat a subject that has or is at risk of having an infection from a pathogen of interest (such as the pathogens listed in the summary of terms) that can be treated by opsonophagocytosis of the pathogen of interest by administration of one or more of P4 peptides, and optionally an opsonic antibody and/or complement protein. In some examples, the one or more P4 peptides is administered without an opsonic antibody and or and/or complement protein. In particular examples, the method includes screening a subject having, thought to have, or at risk of having (for example due to impaired immunity, physiological status, or exposure to a pathogen) a pathogenic infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, a subject is selected that has a pathogenic infection or is at risk of acquiring a pathogen infection from a pathogen that does not express pneumococcal surface adhesin A (PsaA), for example the subject does not have a *Streptococcus pneumoniae* infection. Subjects found to (or known to) have a pathogenic infection and thereby treatable by administration of P4 peptide are selected to receive P4 peptide. Subjects may also be selected who are at risk of developing a pathogenic infection for example, the elderly, the immunocompromised and the very young, such as infants.

Subjects selected for treatment can be administered a therapeutic amount of P4 peptide. The P4 peptide can be administered at doses of 1 µg/kg body weight to about 1 mg/kg body weight per dose, such as 1 µg/kg body weight –100 µg/kg body weight per dose, 100 µg/kg body weight –500 µg/kg body weight per dose, or 500 µg/kg body weight—1000 µg/kg body weight per dose or even greater. However, the particular dose can be determined by a skilled clinician. The agent can be administered in several doses, for example continuously, daily, weekly, or monthly.

The mode of administration can be any used in the art. The amount of agent administered to the subject can be determined by a clinician, and may depend on the particular subject treated. Specific exemplary amounts are provided herein (but the disclosure is not limited to such doses).

Example 4

Treatment of Subjects with P4 Peptide and Opsonic Antibodies

This example describes methods that can be used to treat a subject that has or is at risk of having an infection from a pathogen of interest (such as the pathogens listed in the summary of terms) that can be treated by opsonophagocytosis of the pathogen of interest by administration of one or more of P4 peptides and an opsonic antibody that specifically binds an antigen present on the surface of the pathogen of interest. In particular examples, the method includes screening a subject having, thought to have or at risk of having a pathogenic infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, subjects are screened to identify a particular pathogen of interest, with a serological test, or with a nucleic acid probe specific for a pathogen of interest, or even a panel of nucleic acid probes, such as an array, that can identify several pathogens simultaneously. Subjects found to (or known to) have a pathogenic infection from a pathogen of interest, for example *Streptococcus pneumoniae, Streptococcus pyogenes, Neisseria meningitides* or *Staphylococcus aureus*, such as methicillin resistant *Staphylococcus aureus* (MRSA), and thereby treatable by administration of P4 peptide in conjunction with a opsonic antibody specific for the detected pathogen of interest are selected for administration of P4 peptide and the opsonic antibody specific for the pathogen of interest. Subjects may also be selected who are at risk of developing a pathogenic infection for example, subjects exposed to a known pathogen of interest, the elderly, the immunocompromised and the very young, such as infants.

Subjects selected for treatment can be administered a therapeutic amount of P4 peptide. The P4 peptide can be administered at doses of 1 µg/kg body weight to about 1 mg/kg body weight per dose, such as 1 µg/kg body weight –100 µg/kg body weight per dose, 100 µg/kg body weight –500 µg/kg body weight per dose, or 500 µg/kg body weight –1000 µg/kg body weight per dose. Subjects are administered a therapeutic amount of opsonic antibody that is specific for the identified pathogen of interest. The opsonic antibody can be administered at doses of 1 µg/kg body weight to about 1 mg/kg body weight per dose, such as 1 µg/kg body weight –100 µg/kg body weight per dose, 100 µg/kg body weight –500 µg/kg body weight per dose, or 500 µg/kg body weight –1000 µg/kg body weight per dose. However, the particular dose can be determined by a skilled clinician. The P4 peptide can be administered concurrently or sequentially with opsonic antibody. The P4 peptide and/or the opsonic antibody can be administered in one or several doses, for example continuously, daily, weekly, or monthly. When administered sequentially the time separating the administration of the P4 peptide and opsonic antibody can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

Example 5

Treatment of Subjects with a Combination of Antibiotics, P4 Peptide and Opsonic Antibodies This example describes methods that can be used to treat a subject that has or is at risk of having an infection from a pathogen of interest (such as the pathogens listed in the summary of terms) that can be treated by opsonophagocytosis of the pathogen of interest by administration of one or more of P4 peptides and an opsonic antibody that specifically binds an antigen present on the surface of the pathogen of interest. In particular examples, the method includes screening a subject having, thought to have or at risk of having a pathogenic infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, subjects are screened to identify a particular pathogen of interest, with a serological test, or with a nucleic acid probe specific for a pathogen of interest, or even a panel of nucleic acid probes, such as an array, that can identify several pathogens simultaneously. Subjects found to (or known to) have a pathogenic infection from a pathogen of interest, for example *Streptococcus pneumoniae, Streptococcus pyogenes, Neisseria meningitides* or *Staphylococcus aureus*, such as methicillin resistant *Staphylococcus aureus* (MRSA), and thereby treatable by administration of P4 peptide in conjunction with antibiotics and a opsonic antibody specific for the detected pathogen of interest are selected for administration of P4 peptide the antibiotic and the opsonic antibody specific for the pathogen of interest. Subjects may also be selected who are at risk of developing a pathogenic infection for example, subjects exposed to a known pathogen of interest, the elderly, the immunocompromised and the very young, such as infants.

Subjects selected for treatment are administered a therapeutic amount of P4 peptide. The P4 peptide can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose. Subjects are administered a therapeutic amount of opsonic antibody that is specific for the identified pathogen of interest. The opsonic antibody can be administered at doses of 1 µg/kg body weight to about 1 mg/kg body weight per dose, such as 1 µg/kg body weight-100 µg/kg body weight per dose, 100 µg/kg body weight-500 µg/kg body weight per dose, or 500 µg/kg body weight-1000 µg/kg body weight per dose. However, the particular dose can be determined by a skilled clinician. Subjects selected for treatment are administered a therapeutic amount of P4 peptide. The antibiotic can be administered at doses of 1 µg/kg body weight to about 1 mg/kg body weight per dose (depending upon such factors as the strength and/or type of antibiotic), such as 1 µg/kg body weight-100 µg/kg body weight per dose, 100 µg/kg body weight-500 µg/kg body weight per dose, or 500 µg/kg body weight-1000 µg/kg body weight per dose. The P4 peptide can be administered concurrently or sequentially with the antibiotic and opsonic antibody.

The mode of administration can be any used in the art. The amount of agent administered to the subject can be determined by a clinician, and may depend on the particular subject treated. Specific exemplary amounts are provided herein (but the disclosure is not limited to such doses).

Example 6

Treatment of Subjects with P4 Peptide and Antibiotic

This example describes methods that can be used to treat a subject that has or is at risk of having an infection from a pathogen of interest (such as the pathogens listed in the summary of terms) that can be treated by opsonophagocytosis of the pathogen of interest by administration of one or more of P4 peptides and an opsonic antibody that specifically binds an antigen present on the surface of the pathogen of interest. In particular examples, the method includes screening a subject having, thought to have or at risk of having a pathogenic infection. Subjects of an unknown infection status can be examined to determine if they have an infection, for example using serological tests, physical examination, enzyme-linked immunosorbent assay (ELISA), radiological screening or other diagnostic technique known to those of skill in the art. In some examples, subjects are screened to identify a particular pathogen of interest, with a serological test, or with a nucleic acid probe specific for a pathogen of interest, or even a panel of nucleic acid probes, such as an array, that can identify several pathogens simultaneously. Subjects found to (or known to) have a pathogenic infection from a pathogen of interest, for example *Streptococcus pneumoniae, Streptococcus pyogenes, Neisseria meningitides* or *Staphylococcus aureus*, such as methicillin resistant *Staphylococcus aureus* (MRSA), and thereby treatable by administration of P4 peptide in conjunction with an antibiotic specific for the detected pathogen of interest are selected for administration of P4 peptide and the antibiotic specific for the pathogen of interest. Subjects may also be selected who are at risk of developing a pathogenic infection for example, subjects exposed to a known pathogen of interest, the elderly, the immunocompromised and the very young, such as infants.

Subjects selected for treatment are be administered a therapeutic amount of P4 peptide. The P4 peptide can be administered at doses of 1 µg/kg body weight to about 1 mg/kg body weight per dose, such as 1 µg/kg body weight −100 µg/kg body weight per dose, 100 µg/kg body weight −500 µg/kg body weight per dose, or 500 µg/kg body weight −1000 µg/kg body weight per dose. Subjects are administered a therapeutic amount of opsonic antibody that is specific for the identified pathogen of interest. The antibiotic can be administered at doses of 1 µg/kg body weight to about 1 mg/kg body weight per dose, such as 1 µg/kg body weight −100 µg/kg body weight per dose, 100 µg/kg body weight −500 µg/kg body weight per dose, or 500 µg/kg body weight −1000 µg/kg body weight per dose. However, the particular dose can be determined by a skilled clinician. The P4 peptide can be administered concurrently or sequentially with antibiotic. The P4 peptide and/or the antibiotic can be administered in one or several doses, for example continuously, daily, weekly, or monthly. When administered sequentially the time separating the administration of the P4 peptide and antibiotic can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

Example 7

Treatment of Subjects at Risk for Pneumonia with P4 Peptide

This example describes methods that can be used to treat a subject that has or is at risk of having of pneumonia, for example from a pathogen that is known to cause pneumonia, such as *Streptococcus pneumonia*. In particular examples, the method includes screening a subject having, thought to have or at risk of having a pathogenic infection that causes pneumonia, such as pneumococcal disease, for example infection with *Streptococcus pneumonia*. Subjects may be selected who are at risk of developing a pathogenic infection for example, subjects exposed to a known pathogen of interest, the elderly, the immunocompromised (for example those on immunosupressive therapies or infected with HIV) and the very young, such as infants. An increased risk of pneumococcal infection, such as infection with *Streptococcus pneumoniae* can be associated with defects in the non-specific and specific defense mechanisms against colonization, aspiration or invasion by *Streptococcus pneumoniae*. Examples of such defects include decreased cough reflex, poor cilliary function, and immune deficiencies such as hypogammaglobulinemia, complement defects, leukopenia, or asplenia. Other risk factors include dementia, seizure disorders, current tobacco use, such as cigarette use, alcohol use, congestive heart failure, cereberovascular disease, institutionalization, and chronic obstructive pulmonary disease (COPD). In subjects with asplenia for example the risk of invasive pneumococcal disease is about 500 per 100,000 per year.

Subjects selected for treatment can be administered a therapeutic amount of P4 peptide. The P4 peptide can be administered at doses of 1 μg/kg body weight to about 1 mg/kg body weight per dose, such as 1 μg/kg body weight –100 μg/kg body weight per dose, 100 μg/kg body weight –500 μg/kg body weight per dose, or 500 μg/kg body weight –1000 μg/kg body weight per dose. In some examples, subjects are also administered a therapeutic amount of opsonic antibody that is specific for the identified pathogen of interest. The opsonic antibody can be administered at doses of 1 μg/kg body weight to about 1 mg/kg body weight per dose, such as 1 μg/kg body weight –100 μg/kg body weight per dose, 100 μg/kg body weight –500 μg/kg body weight per dose, or 500 μg/kg body weight –1000 μg/kg body weight per dose. However, the particular dose can be determined by a skilled clinician. The P4 peptide can be administered concurrently or sequentially with opsonic antibody. The P4 peptide and/or the opsonic antibody can be administered in one or several doses, for example continuously, daily, weekly, or monthly. When administered sequentially the time separating the administration of the P4 peptide and opsonic antibody can be seconds, minutes, hours, days, or even weeks.

The mode of administration can be any used in the art. The amount of agent administered to the subject can be determined by a clinician, and may depend on the particular subject treated. Specific exemplary amounts are provided herein (but the disclosure is not limited to such doses).

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

We claim:

1. A therapeutic composition comprising,
   a therapeutically effective amount of an isolated P4 peptide consisting of the amino acid sequence set forth as SEQ ID NO: 1; and
   a therapeutically effective amount of one or more exogenous isolated opsonic antibodies or a fragment thereof that specifically binds to an antigen present on the surface of a bacterial pathogen of interest, wherein the bacterial pathogen of interest is a bacterial pathogen comprising *Streptococcus pneumoniae, Neisseria meningitides, Streptococcus pyogenes*, or *Staphylococcus aureus*; and
   a therapeutically effective amount isolated complement protein or fragment thereof.

2. The therapeutic composition of claim 1 further comprising a therapeutically effective amount of an antibiotic for the pathogen of interest.

3. The composition of claim 1, wherein the composition is formulated for intranasal, intravenous, topical, enteral, parenteral, or intravitreal administration.

4. The composition of claim 1, wherein the one or more exogenous isolated opsonic antibodies or a fragment thereof comprise gamma globulin.

* * * * *

```
SEQUENCE LISTING

<160> NUMBER OF SEQ ID NOS: 1

<210> SEQ ID NO 1
<211> LENGTH: 28
<212> TYPE: PRT
<213> ORGANISM: Artificial Sequence
<220> FEATURE:
<223> OTHER INFORMATION: Synthetic P4 peptide sequence.

<400> SEQUENCE: 1

Leu Phe Val Glu Ser Ser Val Lys Arg Arg Pro Met Lys Thr Val Ser
1               5                   10                  15

Gln Asp Thr Asn Ile Pro Ile Tyr Ala Gln Ile Phe
            20                  25
```